US011020283B2

(12) United States Patent
Manabe et al.

(10) Patent No.: US 11,020,283 B2
(45) Date of Patent: Jun. 1, 2021

(54) METHOD AND DEVICE FOR MANUFACTURING ABSORBER

(71) Applicant: DAIO PAPER CORPORATION, Ehime (JP)

(72) Inventors: Sadanao Manabe, Tokyo (JP); Ryoichi Ochi, Ehime (JP)

(73) Assignee: DAIO PAPER CORPORATION, Ehime (JP)

( * ) Notice: Subject to any disclaimer, the term of this patent is extended or adjusted under 35 U.S.C. 154(b) by 135 days.

(21) Appl. No.: 16/088,916

(22) PCT Filed: Feb. 23, 2017

(86) PCT No.: PCT/JP2017/006710
§ 371 (c)(1),
(2) Date: Sep. 27, 2018

(87) PCT Pub. No.: WO2017/169340
PCT Pub. Date: Oct. 5, 2017

(65) Prior Publication Data
US 2019/0125592 A1    May 2, 2019

(30) Foreign Application Priority Data
Mar. 30, 2016    (JP) .............................. JP2016-069155

(51) Int. Cl.
*A61F 13/15*    (2006.01)
*A61F 13/532*    (2006.01)
(Continued)

(52) U.S. Cl.
CPC ........ *A61F 13/15804* (2013.01); *A61F 13/15* (2013.01); *A61F 13/15658* (2013.01);
(Continued)

(58) Field of Classification Search
CPC ................ A61F 13/15804; A61F 13/15; A61F 13/15658; A61F 13/15674;
(Continued)

(56) References Cited

U.S. PATENT DOCUMENTS 4,041,203 A * 8/1977 Brock ...................... B32B 5/08
428/157
2007/0116926 A1    5/2007 Hoying et al.
(Continued)

FOREIGN PATENT DOCUMENTS

JP    1988283777 A    11/1988
JP    2007130819 A    5/2007
(Continued)

OTHER PUBLICATIONS

International Search Report for PCT/JP2017/006710, dated May 16, 2017.

*Primary Examiner* — Michael A Tolin
(74) *Attorney, Agent, or Firm* — Andrus Intellectual Property Law, LLP

(57) ABSTRACT

A manufacturing device is provided, within a range in the rotation direction of the upper half of an anvil roll, in the order from the upstream side in the rotation direction of the anvil roll, with a first sheet feeding unit, a recess forming unit, a particulate material feeding device, and a second sheet feeding unit and further a welding unit provided on the downstream side of the second sheet feeding unit in the rotation direction. The anvil roll has a large number of concaves, projections provided in a portion among the concaves, so as to surround each of the concaves, and a unit to suck air in the concaves. For each concave, the projections are minute dot-shaped projections arranged only in one row at intervals in the direction surrounding the concave.

7 Claims, 28 Drawing Sheets

(51) Int. Cl.
  *B29C 59/02* (2006.01)
  *B29C 65/08* (2006.01)
  *B29C 59/00* (2006.01)
  *B29C 65/00* (2006.01)
  *A61F 13/53* (2006.01)
  *B29L 31/48* (2006.01)

(52) U.S. Cl.
  CPC .. *A61F 13/15674* (2013.01); *A61F 13/15731* (2013.01); *A61F 13/15739* (2013.01); *A61F 13/15764* (2013.01); *A61F 13/5323* (2013.01); *B29C 59/002* (2013.01); *B29C 59/022* (2013.01); *B29C 65/08* (2013.01); *B29C 66/729* (2013.01); *A61F 2013/15869* (2013.01); *A61F 2013/15878* (2013.01); *A61F 2013/15926* (2013.01); *A61F 2013/530562* (2013.01); *B29K 2995/0068* (2013.01); *B29L 2031/4878* (2013.01)

(58) Field of Classification Search
  CPC .......... A61F 13/15731; A61F 13/15739; A61F 13/15764; A61F 2013/15869; A61F 2013/15878; A61F 2013/15926; A61F 13/15707; A61F 13/5323; A61F 13/539; A61F 2013/15715; A61F 2013/15861; A61F 2013/15886; A61F 2013/15902; A61F 2013/530481; A61F 2013/53051; A61F 2013/530547; A61F 2013/530554; A61F 2013/530562; A61F 2013/530591; A61F 2013/5395; A61F 2013/53991; B29C 59/002; B29C 59/022; B29C 65/08; B29C 66/729; B29C 55/08; B29C 59/04; B29C 59/06; B29C 65/20; B29K 2995/0068; B29L 2031/4878; B32B 5/16; B32B 5/30; B32B 37/0076; B32B 37/0084; B32B 37/24; B32B 38/0012; B32B 38/1858; B32B 2038/0028; B32B 2555/02
  USPC ........................................................ 156/242
  See application file for complete search history.

(56) References Cited

U.S. PATENT DOCUMENTS

| | | | |
|---|---|---|---|
| 2010/0051166 A1 | 3/2010 | Hundorf et al. | |
| 2010/0100065 A1 | 4/2010 | Bianco et al. | |
| 2013/0284361 A1 | 10/2013 | Tsujimoto et al. | |
| 2014/0008024 A1 | 1/2014 | Ogasawara et al. | |
| 2015/0144270 A1 | 5/2015 | Nakakado | |
| 2015/0164699 A1* | 6/2015 | Schmitz | B29C 66/83411 428/201 |
| 2016/0250083 A1* | 9/2016 | Tsujimoto | B29C 66/433 604/385.01 |

FOREIGN PATENT DOCUMENTS

| | | |
|---|---|---|
| JP | 2010522595 A | 7/2010 |
| JP | 2012500669 A | 1/2012 |
| JP | 2012147957 A | 8/2012 |
| JP | 2013017565 A | 1/2013 |
| WO | 2012108331 A | 8/2012 |
| WO | 2015072347 A | 3/2017 |

\* cited by examiner

METHOD AND DEVICE FOR MANUFACTURING ABSORBER

CROSS-REFERENCE TO RELATED APPLICATIONS

This application is the U.S. national stage application of International Application PCT/JP2017/006710, filed Feb. 23, 2017, which international application was published on Oct. 5, 2017, as International Publication WO 2017/169340 in the Japanese language. The International Application claims priority of Japanese Patent Application No. 2016-069155, filed Mar. 30, 2016. The international application and Japanese application are both incorporated herein by reference, in entirety.

TECHNICAL FIELD

The present invention relates to a device and a method for manufacturing an absorber to be used for an absorbent article, such as disposable diapers and sanitary napkins.

BACKGROUND ART

The absorbent article includes an absorbent and a liquid-pervious top sheet covering the front surface side of the absorber. Excretion liquid such as urine and menstrual blood passes through the top sheet and is absorbed and held by the absorber. An absorber obtained by mixing superabsorbent polymer (SAP) particles with hydrophilic short fibers such as fluff pulp and being accumulated in a cotton form has been widely used. However, while ensuring a sufficient absorbable amount and in response to the request for further thinning, weight reduction, and cost reduction, various types of absorbers (hereinafter also referred to as cell absorbers) are proposed. Such absorber includes a large number of cells (small chambers) which are surrounded by bonded portions of the front surface side sheet and the back surface side sheet, and these sheets are not bonded in each cell. Further, the cell contains particulate materials including superabsorbent polymer particles (refer to, for example, Patent Literatures 1 to 7 below).

Various manufacturing methods for the cell absorbers have been proposed (for example, refer to Patent Literatures 1 to 7 below). However, the methods are basically common in: forming a large number of receiving recesses at intervals in the transfer process thereof while continuously transferring the first sheet to be one of the front surface side sheet and the back surface side sheet; then, feeding the particulate materials including the superabsorbent polymer particles into the receiving recesses; subsequently, covering a second sheet on the opening side of the receiving recesses of the first sheet; bonding portions among the receiving recesses of the first sheet and the second sheet; and then cutting these bonded sheets intermittently at positions to be boundaries between the individual absorbers.

However, for example, in the case of manufacturing the absorber by the method described in Patent Literature 3, when the portions among the recesses of the first sheet and the second sheet are bonded, if the particulate materials are present between the first sheet and the second sheet at the bonded portions, bonding failure (including both of the case where portions to be bonded have low bonding strength and the case where the portions are not bonded at all) may occur.

For this problem, in the invention disclosed in Patent Literature 1, a technique is proposed in which a large number of suction holes are provided on a conveying surface of a roll on the first sheet side, discharge ports are provided between the respective adjacent suction holes, recesses are formed in the first sheet by suction with the suction holes, and particulate materials are fed on the first sheet while emitting air from the discharge ports. However, in this method, it is necessary to provide the air discharge ports in projections forming the bonded portions, and therefore there is a problem that the arrangement and shape of the projections are limited. In addition, obviously the manufacturing facilities become complicated.

CITATION LIST

Patent Literature

Patent Literature 1: WO/2012/108331
Patent Literature 2: JP 2012-147957 A
Patent Literature 3: JP 2007-130819 A
Patent Literature 4: JP 63-283777 A
Patent Literature 5: JP 2013-17565 A
Patent Literature 6: JP 2012-500669 A
Patent Literature 7: JP 2010-522595 A

SUMMARY OF INVENTION

Technical Problem

In view of the above, the main object of the present invention is to prevent bonding failure of the sheets by a further simple method without restriction on the arrangement and shape of the projections (in other words, bonded portions) of the anvil roll in manufacturing the cell absorbers.

Solution to Problem

The representative aspects of the present invention that have solved the above problems will be described below.
<First Aspect>
A device for manufacturing an absorber, comprising:
an anvil roll, which has a plurality of concaves arranged at intervals on an outer peripheral surface, projections provided in a portion among the concaves, so as to surround each of the concaves, a suction unit configured to suck air in the concaves, without a suction port or discharge port in the portion among the concaves, and which is rotationally driven around a transverse rotational axis, and
the device further comprising a first sheet feeding unit, a receiving recess forming unit, a particulate material feeding device, a second sheet feeding unit and a welding unit in this order from the upstream side in the rotation direction of the anvil roll within a range in the rotation direction of the upper half of the anvil roll,
the first sheet feeding unit being configured to feed a continuous belt-shaped first sheet made of a liquid pervious nonwoven fabric in the rotation direction of the anvil roll along the outer peripheral surface of the anvil roll;
the receiving recess forming unit being configured to form receiving recesses in the first sheet along the outer peripheral surface of the anvil roll, the receiving recesses being recessed in the concaves;
the particulate material feeding device being configured to drop and feed particulate materials including superabsorbent polymer particles from above to the receiving recesses of the first sheet wound around the anvil roll;
the second sheet feeding unit being configured to feed a continuous belt-shaped second sheet in the rotation direction of the anvil roll, wind the second sheet around the outer side of the first sheet, and cover at least a range in the cross direction (CD) having the receiving recesses of the first sheet, with the second sheet; and the welding unit being configured to weld the first sheet and the second sheet only at the projections while winding the first sheet and the second sheet around the anvil roll, and being provided on the downstream side of the second sheet feeding unit in the rotation direction of the anvil roll, wherein the suction unit sucks air in the concaves at least in a range in the rotation direction from a feeding position of the particulate materials to a feeding position of the second sheet, as the projections, dot-shaped projections are arranged only in one row at intervals in the direction surrounding each of the concaves, the area of the tip end surface of each dot-shaped projection is 8 mm.sup.2 or less, the width in the direction orthogonal to the arrangement direction is 4 mm or less, and peripheral edges of the receiving recesses in the first sheet coincide with the edges on the receiving recess side of the dot-shaped projections surrounding the receiving recesses.

(Function and Effect)

In such configuration where on the outer peripheral surface of the anvil roll for bonding the first sheet and the second sheet by welding, prior to bonding, forming of the receiving recesses of the first sheet, feeding of the particulate materials, and covering with the second sheet are performed. At least from feeding of the particulate materials to covering with the second sheet, a basic mode is carried out where the inside of each concave of the anvil roll is sucked. The projections of the anvil roll are intentionally set to small dot-shaped projections and provided in a portion among the concaves only in one row at intervals in the direction surrounding each of the concaves. The peripheral edge of each receiving recess in the first sheet coincides with the edges on the receiving recess side of the dot-shaped projections surrounding the receiving recess. In this case, since the projections have small dot shapes, it is basically difficult for the particulate materials to be placed on the positions overlapping the projections of the anvil roll in the first sheet. In addition, since each receiving recess formed in the first sheet becomes a receiving recess which is inclined from the inner edges of the projections surrounding the concave, the particulate materials easily drop in the receiving recess by suction force, and the particulate materials are likely to move to a deeper position. Furthermore, for each receiving recess, in the portion between each pair of the dot-shaped projections adjacent to each other in the direction surrounding the concave, the first sheet is inclined toward the low point at the center of the adjacent projections and inclined toward the receiving recesses on the both sides of the portion (like a ridge of connected mountains), such that the particulate materials positioned in the dot-shaped projections or in the vicinity thereof are more likely to move toward the inside of the receiving recesses by the suction force. Therefore, the first sheet and the second sheet are bonded by welding in a simple technique of changing the pattern of the projections of the anvil roll, which makes it harder for the particulate materials to get caught between the sheets at the bonded portions, and bonding failure of the sheets can be effectively prevented.

<Second Aspect>

The device for manufacturing an absorber according to the first aspect, comprising, as the receiving recess forming unit, a pushing roll which is opposed to the anvil roll, and which has push-in pins for entering the respective concaves of the anvil roll, wherein a continuous belt-shaped first sheet is passed in the rotation direction of the anvil roll between the anvil roll and the push-in roll, and the first sheet is pushed into the concaves with the push-in pins to form the receiving recesses in the first sheet.

(Function and Effect)

When the receiving recesses are formed by such a push-in roll, the receiving recesses are formed more firmly. Therefore, it is preferable because the particulate materials more easily drop into the receiving recesses.

<Third Aspect>

The device for manufacturing an absorber according to the first or second aspect, comprising a wave-forming device including, a groove roll having a plurality of grooves continuing in the roll circumferential direction and being arranged in the roll length direction on the outer peripheral surface of the groove roll, a convex roll having a plurality of continuous convex portions continuing in the roll circumferential direction and being arranged in the roll length direction on the outer peripheral surface of the convex roll, and a heating unit wherein the groove roll and the convex roll being opposed to each other such that the grooves and the continuous convex portions are engaged with each other, and the heating unit heats the first sheet, which passes through between the groove roll and the convex roll, to a melting temperature or lower, wherein the first sheet is passed through between the groove roll and the convex roll of the wave-forming device so that the first sheet is softened by stretching in a waveform in the CD while being heated, and then, the first sheet is fed to the anvil roll by the first sheet feeding unit.

(Function and Effect)

If the first sheet is pretreated by such a wave-forming device, the first sheet is softened and becomes stretchable by the change in the fiber structure due to stretching of the first sheet. Therefore, the receiving recesses can be formed further firmly in forming the receiving recesses, in addition to this, the first sheet is firmly sucked into the concaves by suction such that the first sheet becomes to have a surface shape further easier to drop in the receiving recesses, and thus this aspect is preferable.

<Fourth Aspect>

The device for manufacturing an absorber according to the third aspect, wherein the pushing depth of the first sheet by the push-in pin is 2 to 10 mm, and in the wave-forming by the wave-forming device, the wave height is 1 to 8 mm, and the peak-to-peak interval in the CD is 1 to 5 mm (Function and Effect)

To what extent the receiving recess are formed by the push-in roll and to what extent the wave-forming is performed can be appropriately determined, but in the usual case, it is desirable to set them within such a range.

<Fifth Aspect>

The device for manufacturing an absorber according to the first to fourth aspects, wherein the feeding position of the particulate materials by the particulate material feeding device is disposed in a range having the rotation angle, with the vertically upward direction as 0.degree., of 30.degree. or more, and an angle formed by a horizontal plane and a ridge line positioned on the most downstream side in the rotation direction of the receiving recess of the first sheet is 0.degree. or more.

(Function and Effect)

When the particulate materials are dropped and fed onto the first sheet at such a position, even if the particulate materials drop to a position corresponding to the projection of the anvil roll in the first sheet, the particulate materials are likely to drop on the downstream side in the rotation direction, such that the particulate materials do not easily stay at the position corresponding to the projection. Further, the receiving recess is oriented sideways, which makes difficult to cause a situation in which the particulate materials in the receiving recess to move to the position corresponding to the projection of the anvil roll.

<Sixth Aspect>

A method for manufacturing an absorber using manufacturing device which comprises:

an anvil roll, which has a plurality of concaves arranged at intervals on an outer peripheral surface, projections provided in a portion among the concaves, so as to surround each of the concaves, a suction unit configured to suck air in the concaves, without a suction port or discharge port in the portion among the concaves, and which is rotationally driven around a transverse rotational axis, the device further comprising a first sheet feeding unit, a receiving recess forming unit, a particulate material feeding device, a second sheet feeding unit and a welding unit in this order from the upstream side in the rotation direction of the anvil roll within a range in the rotation direction of the upper half of the anvil roll, the first sheet feeding unit being configured to feed a continuous belt-shaped first sheet made of a liquid pervious nonwoven fabric in the rotation direction of the anvil roll along the outer peripheral surface of the anvil roll;

the receiving recess forming unit being configured to form receiving recesses in the first sheet along the outer peripheral surface of the anvil roll, the receiving recesses being recessed in the concaves;

the particulate material feeding device being configured to drop and feed particulate materials including superabsorbent polymer particles from above to the receiving recesses of the first sheet wound around the anvil roll;

the second sheet feeding unit being configured to feed a continuous belt-shaped second sheet in the rotation direction of the anvil roll, wind the second sheet around the outer side of the first sheet, and cover at least a range in the CD having the receiving recesses of the first sheet, with the second sheet; and the welding unit being configured to weld the first sheet and the second sheet only at the projections while winding the first sheet and the second sheet around the anvil roll, and being provided on the downstream side of the second sheet feeding unit in the rotation direction of the anvil roll, wherein the suction unit sucks air in the concaves at least in a range in the rotation direction from a feeding position of the particulate materials to a feeding position of the second sheet, as the projections, dot-shaped projections are arranged only in one row at intervals in the direction surrounding each of the concaves, the area of the tip end surface of each dot-shaped projection is 8 mm.sup.2 or less, the width in the direction orthogonal to the arrangement direction is 4 mm or less, and peripheral edges of the receiving recesses in the first sheet coincide with the edges on the receiving recess side of the dot-shaped projections surrounding the receiving recesses, and the method comprising:

feeding the first sheet to the anvil roll by the first sheet feeding unit;

forming the receiving recesses on the first sheet by the receiving recess forming unit;

feeding the particulate materials to the receiving recesses of the first sheet by the particulate material feeding device;

overlapping the second sheet on the first sheet by the second sheet feeding unit;

bonding the portions among the receiving recesses of the first sheet and the second sheet by the welding unit to successively form a continuous series of the absorbers in which a plurality of cells containing the particulate materials are arranged; and cutting the continuous series of the absorbers into individual absorbers at intervals in the machine direction (MD).

(Function and Effect)

The same functions and effects as those obtained in the first aspect are obtained.

Advantage Effects of Invention

According to the present invention, it is advantageous that bonding failure of the sheets can be prevented by a further simple method without restriction on the arrangement and shape of the protrusions (in other words, bonded portions) of the anvil roll in manufacturing the cell absorber.

DESCRIPTION OF EMBODIMENTS

Figure 1:
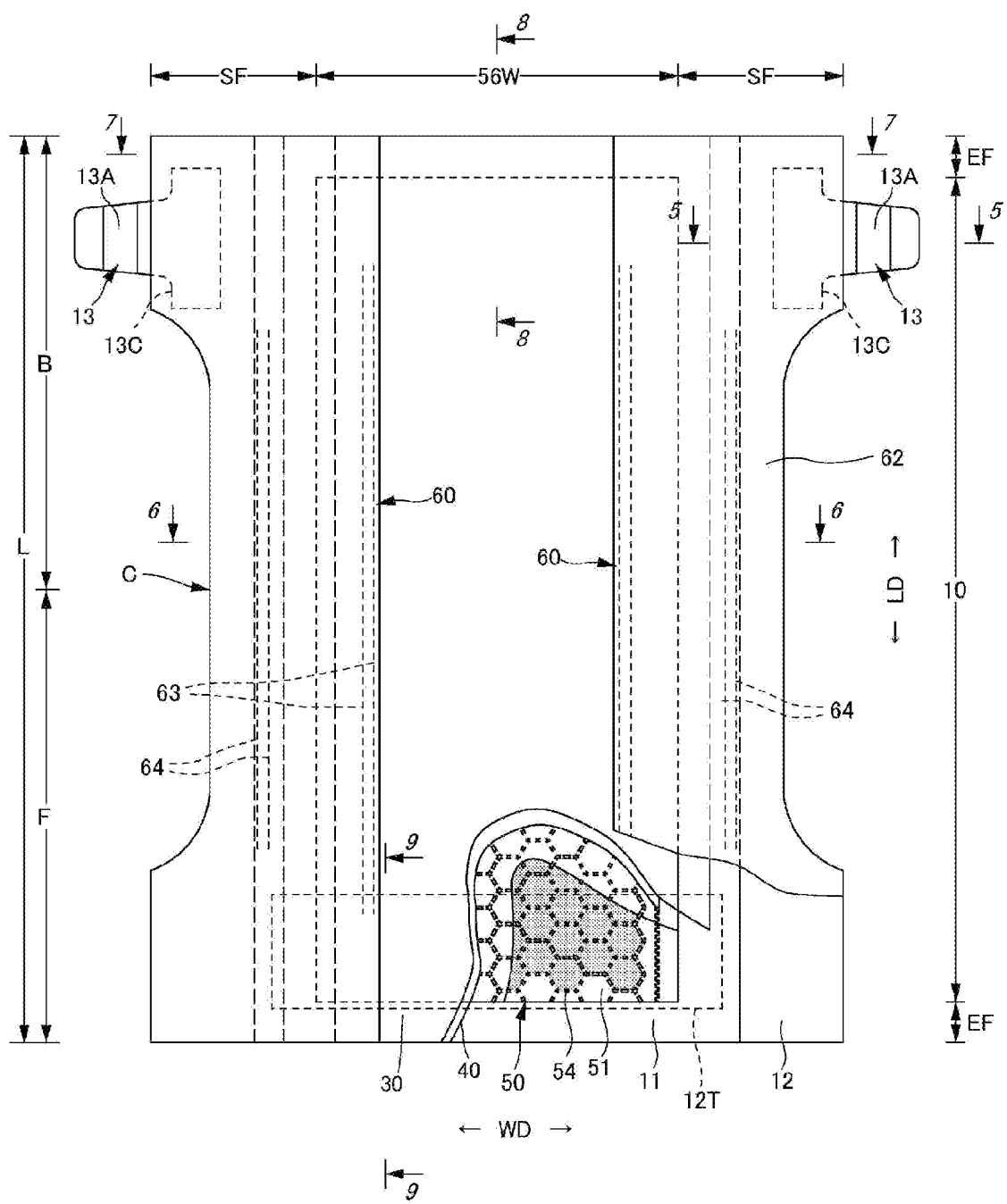
FIG. 1 is a plan view illustrating the inner surface of a tape-type disposable diaper in a state where a diaper is spread.

Hereinafter, embodiments of the present invention will be described with reference to the accompanying drawings.
Example of Absorbent Article FIGS. 1 to 6 illustrate examples of a tape-type disposable diaper, in which the reference sign X indicates the maximum width of the diaper excluding the fastening tapes, and the reference sign L indicates the maximum length of the diaper. Each component member is fixed or bonded in the same manner as known diapers as necessary except for the fixing or bonded portion described below. As a unit for fixing or bonding, a hot melt adhesive or welding (heat welding, ultrasonic welding) can be selected as appropriate.

This tape type disposable diaper has a basic structure in which an absorber 50 is interposed between a liquid pervious top sheet and a liquid impervious sheet located on the external surface side. The tape type disposable diaper includes a ventral side end flap portion EF, a dorsal side end flap portion EF, and a pair of side flap portions SF. The ventral side end flap portion EF and the dorsal side end flap portion EF are portions extending to the front side and the back side of the absorber 50 respectively and not including the absorber 50. The pair of the side flap portions SF extends laterally from the side edges of the absorber 50. In each of the side flap portions SF in a dorsal side portion B, a fastening tape 13 is provided. When a user wears the diaper, the fastening tape 13 is engaged at an appropriate place on the external surface of the ventral side portion F in a state in which the side flap portion SF of the dorsal side portion B is overlaid on the external side of the side flap portion SF of the ventral side portion F.

In this tape type disposable diaper, the entire external surface of the absorbent main unit 10 and the respective side flap portions SF is formed by an outer sheet 12. Particularly, in a region including the absorber 50, a liquid impervious sheet 11 is fixed to the internal surface side of the outer sheet 12 with an adhesive such as a hot melt adhesive. Further, the absorber 50, an intermediate sheet 40, and a top sheet 30 are stacked in this order on the internal surface side of the liquid impervious sheet 11. In the illustrated example, the top sheet 30 and the liquid impervious sheet 11 are rectangular in shape and have somewhat larger sizes in the front-back direction LD and the width direction WD than the absorber 50. The peripheral edge portions protruding from the side edges of the absorber 50 in the top sheet 30 and the peripheral edge portions protruding from the side edges of the absorber 50 in the liquid impervious sheet 11 are bonded by a hot melt adhesive or the like. Further, the liquid impervious sheet 11 is formed to be slightly wider than the top sheet 30.

On the both sides of the absorbent main unit 10, three-dimensional side gathers 60 and 60 projecting (standing) to the skin side of a wearer are provided, and gather sheets 62 and 62 forming the three-dimensional side gathers 60 and 60 are fixed in ranges on the both sides of the top sheet 30 to the inner surfaces of the side flap portions SF.

Details of each part will be described in order below.
(Outer Sheet)

The outer sheet 12 is a sheet constituting the external surface of a product. The outer sheet 12 has a shape in which the intermediate portions in the front-back direction LD on the both side portions are narrowed, and these portions surround the wearer's legs. A nonwoven fabric is suitable for the outer sheet 12, but it is not limited thereto. The type of the nonwoven fabric is not particularly limited. As a raw material fiber, for example, in addition to synthetic fibers such as olefin type such as polyethylene or polypropylene, polyester type, and polyamide type, regenerated fibers such as rayon and cupra, and natural fibers such as cotton can be used. As a processing method, a spun lace method, a spun bond method, a thermal bond method, an air through method, a needle punch method, and the like can be used. However, a long-fiber nonwoven fabric such as a spun-bonded nonwoven fabric, an SMS nonwoven fabric, and an SMMS nonwoven fabric are preferable in that both good texture and strength can be compatible. In addition to using a single piece of nonwoven fabric, it is also possible to use multiple nonwoven fabrics in layers. In the latter case, it is preferable that the nonwoven fabrics are adhered to each other with a hot melt adhesive or the like. When a nonwoven fabric is used, the basis weight of the fiber is desirably 10 to 50 g/m.sup.2, particularly desirably 15 to 30 g/m.sup.2. The outer sheet 12 can be omitted, and in that case, the liquid impervious sheet 11 can have the same shape as that of the outer sheet 12, such that the outer surface of a product can be formed.

(Liquid Impervious Sheet)

Although the material of the liquid impervious sheet 11 is not particularly limited, for example, an olefin resin such as polyethylene or polypropylene, a laminated nonwoven fabric obtained by stacking a nonwoven fabric on a polyethylene sheet or the like, a nonwoven fabric in which liquid permeability is substantially secured through a water proof film (in this case, a liquid impervious sheet is formed by the waterproof film and the nonwoven fabric) can be exemplified. Obviously, besides this, in recent years, liquid impervious and moisture permeable materials which have been favorably used from the standpoint of prevention of stuffiness can also be exemplified. As a sheet of this liquid-impervious and moisture-permeable material, for example, a microporous sheet can be exemplified which is obtained by kneading an olefin resin such as polyethylene resin or polypropylene resin and an inorganic filler, forming a sheet with the kneaded materials and monoaxially or biaxially stretching the sheet. Further, nonwoven fabrics using micro denier fibers and a sheet that is liquid impervious without using a water proof film can also be used as the liquid impervious sheet 11. The sheet has liquid impermeability by having high leak proof by reducing air gaps of fibers by heating or applying pressure and by applying a superabsorbent resin, a hydrophobic resin, or a water repellent agent.

(Top Sheet)

As the top sheet 30, a porous or non-porous nonwoven fabric having liquid permeability can be used. The type of constituent fibers of the nonwoven fabric is not particularly limited. Examples of the nonwoven fabric can include synthetic fibers such as olefin type such as polyethylene and polypropylene, polyester type, and polyamide type, regenerated fibers such as rayon and cupra, natural fibers such as cotton, mixed fibers and conjugate fibers in which two or more of these are used, and the like. Further, the nonwoven fabric may be manufactured by any processing. Examples of processing methods can include known methods such as a spun lace method, a spun bond method, a thermal bond method, a melt blown method, a needle punch method, an air through method, and a point bond method. For example, the spun lace method is preferable when flexibility and drapeability are required, and the thermal bonding method is preferable when bulkiness and softness are required.

(Intermediate Sheet)

The intermediate sheet 40 is bonded to the back surface of the top sheet 30 to promptly move excretion liquid passing through the top sheet 30 to the side of the absorber 50 and to prevent returning. For bonding between the intermediate sheet 40 and the top sheet 30, heat embossing or ultrasonic welding can be used in addition to using a hot melt adhesive. As the intermediate sheet 40, a resin film having a large number of through holes can be used in addition to using a nonwoven fabric. As the nonwoven fabric, a material similar to that described in the section of the top sheet 30 can be used. However, the material having a higher hydrophilicity than that of the top sheet 30 or the material having a high fiber density is preferable since those have excellent liquid transfer characteristics from the top sheet 30 to the intermediate sheet 40.

Although the intermediate sheet 40 in the illustrated embodiment is shorter than the width of the absorber 50 and disposed at the center portion, it may be provided throughout the maximum width. The length of the intermediate sheet 40 in the front-back direction LD may be the same as the maximum length of the diaper, may be the same as the length of the absorber 50, or may be within a short length range around a region receiving a liquid.

(Three-Dimensional Side Gather)

To prevent lateral movement of excrement on the top sheet 30 and to prevent lateral leakage, it is preferable to provide the three-dimensional side gathers 60 projecting (standing) from the inner faces on the both sides of the product in the width direction WD.

Figure 3:
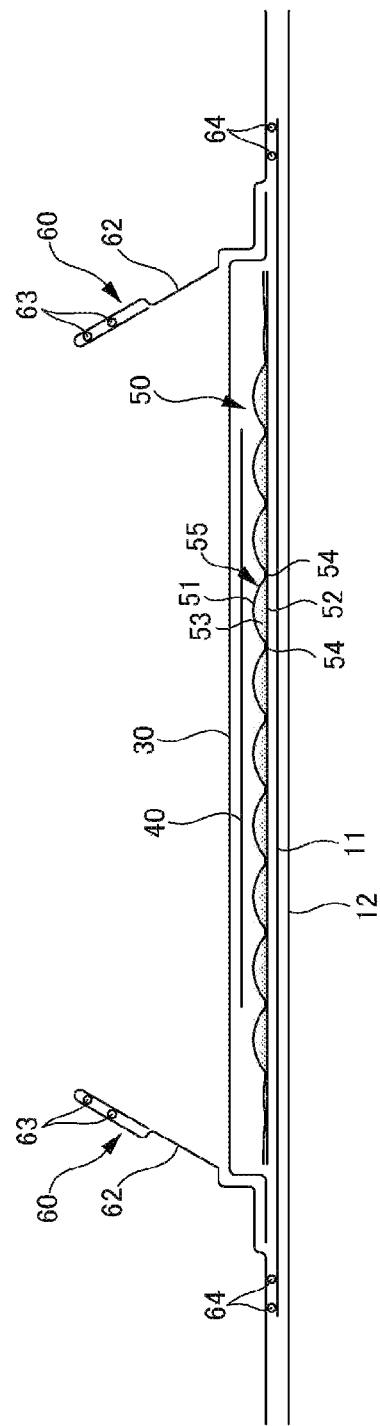
FIG. 3 is a cross-sectional view taken along line 6-6 in FIG. 1.
Figure 4:
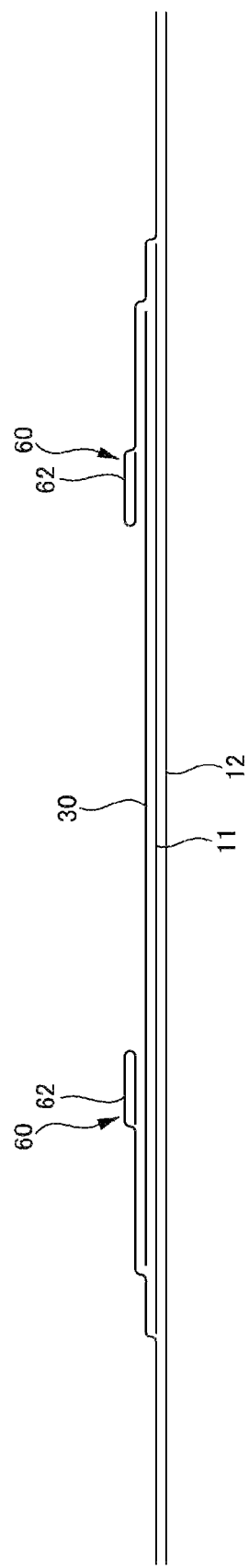
FIG. 4 is a cross-sectional view taken along line 7-7 in FIG. 1.
Figure 5A:
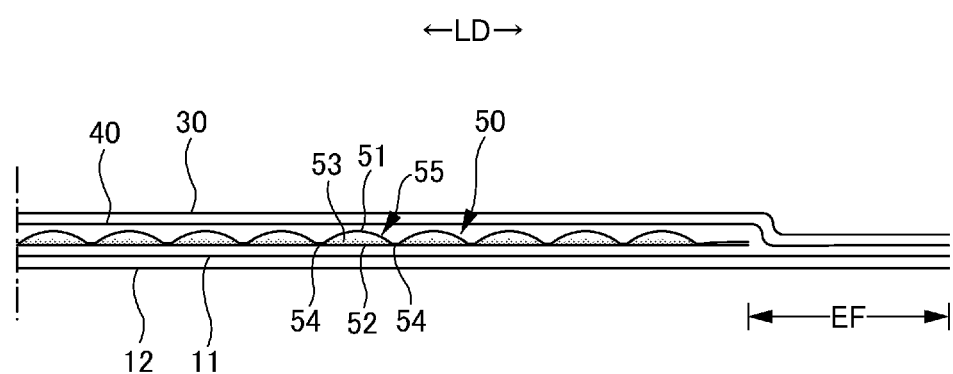
FIG. 5A is a cross-sectional view taken along line 8-8 in FIG. 1.
Figure 5B:
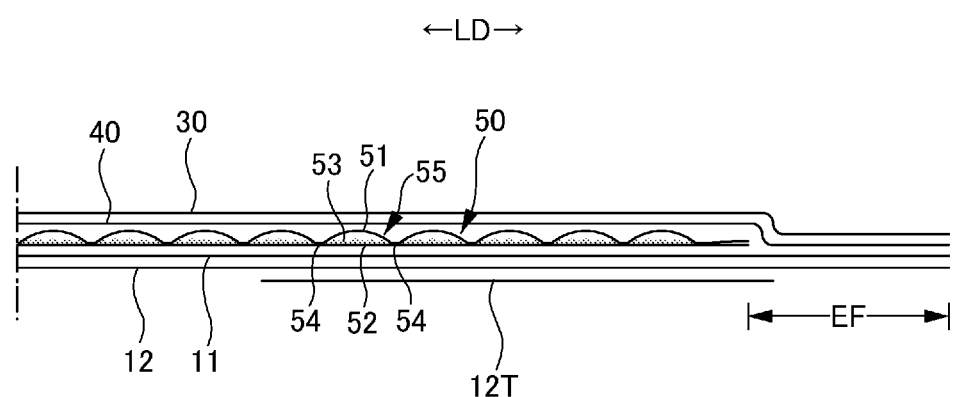
FIG. 5B is a cross-sectional view taken along line 9-9 in FIG. 1.

Each three-dimensional side gather 60 is composed of gather sheet 62 and one or plurality of elongated elastically stretchable members 63 fixed to the gather sheet 62 in a stretched state along the front-back direction LD. As this gather sheet 62, a water repellent nonwoven fabric can be used, and rubber thread and the like can be used as the elastically stretchable member 63. As shown in FIGS. 1 and 3, a plurality of the elastically stretchable members may be provided on each side, or only one elastically stretchable member may be provided on each side.

The inner surface of the gather sheet 62 has a fixed start point in the width direction WD on the side portion of the top sheet 30. A portion outside in the width direction WD from this fixed start point is fixed with a hot melt adhesive or the like on the side portion of the liquid impervious sheet 11 and the side portion of the outer sheet 12 positioned at the outside portion.

In the periphery of the leg, the inside in the width direction WD from the fixed start point of each three-dimensional side gather 60 is fixed on the top sheet 30 at both ends of the product in the front-back direction LD. However, the portion therebetween is a non-fixed free portion erected by contraction force of one or a plurality of the elastically stretchable members 63. Since the diaper is attached to the body in a boat shape in the wearing of the diaper, and the contraction force of one or a plurality of the elastically stretchable members 63 acts, the three-dimensional side gathers 60 erect by the contraction force of one or a plurality of the elastically stretchable members 63 and come in close contact with the legs. As a result, so-called lateral leakage from around the legs is prevented.

Unlike the illustrated embodiment, both end portions in the front-back direction LD in the portion of the inside in the width direction WD of each gather sheet 62 are fixed in a state folded in two having a base end side portion, which extends inward from a portion outside in the width direction WD and a tip side portion, which is folded back on the body side from the end edge on the center side in the width direction WD of the base end side portion and extending outward in the width direction WD, and the portion therebetween may be a non-fixed free portion.

(Flat Gather)

Figure 2:
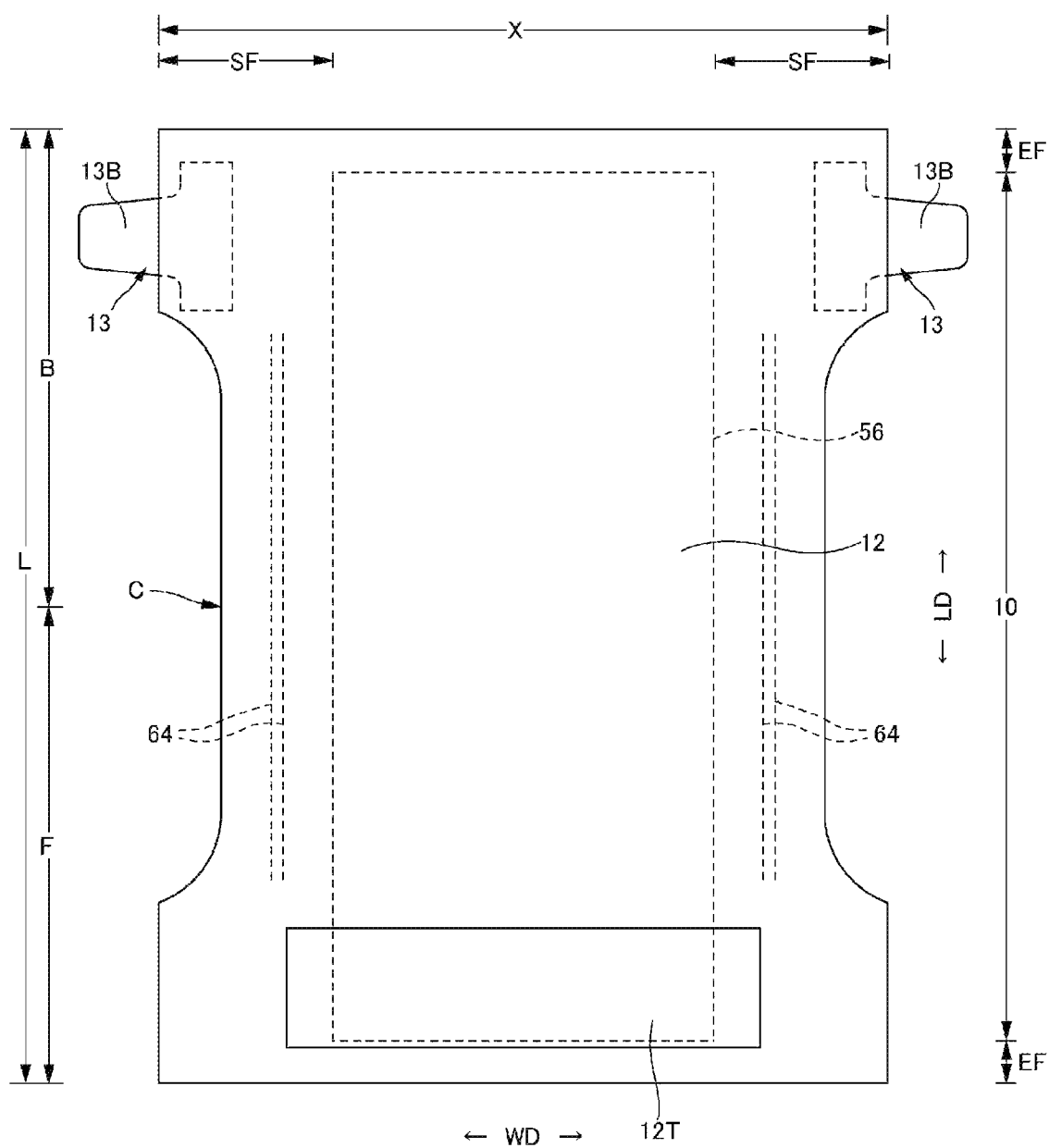
FIG. 2 is a plan view illustrating the outer surface of a tape-type disposable diaper in a state where a diaper is spread.

As illustrated in FIGS. 1 to 3, in each side flap portion SF, on the outside in the width direction WD in the vicinity of the fixed start point of the fixed portion of the gather sheet 62, between the gather sheet 62 and the liquid impervious sheet 11, the elastically stretchable members 64, which are made of rubber threads and the like, around the leg portions are fixed in a state stretching along the front-back direction LD, whereby the leg portion of each side flap portion SF is formed as a flat gather. The elastically stretchable members 64 around each leg portion can also be disposed between the liquid impervious sheet 11 and the outer sheet 12 in the side flap portion SF. As in the illustrated example, a plurality of elastically stretchable members 64 around the leg portions may be provided on each side, or only one elastically stretchable member 64 may be provided on each side.

(Fastening Tape)

Figure 6:
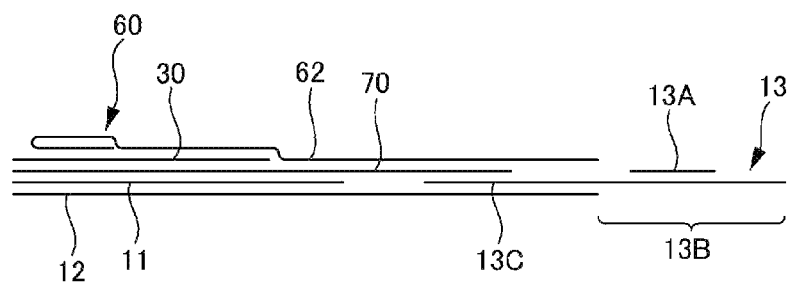
FIG. 6 is a cross-sectional view taken along line 5-5 in FIG. 1.

As illustrated in FIGS. 1, 2, and 6, each fastening tape 13 includes a sheet base material forming a tape attaching portion 13C fixed to the side portion of a diaper and a tape main unit section 13B projecting from the tape attaching portion 13C, and an engagement portion 13A with respect to the ventral side, which is provided in the middle portion in the width direction WD of the tape main unit section 13B in the seat base material. A tip end side from the engagement portion 13A is a tab part. The tape attaching portion 13C of the fastening tape 13 is sandwiched between the gather sheet 62 forming the inner layer in the side flap portion and the outer sheet 12 forming the outer layer and is adhered to the both sheets 62 and 12 with the hot melt adhesive. In addition, the engagement portion 13A is bonded to the sheet base material with an adhesive so that it cannot be removed.

A hook member (male member) of a mechanical fastener (hook and loop fastener) is suitable as the engagement portion 13A. The hook member has a large number of engagement projections on its outer surface side. The engagement projection has a check mark shape, a J shape, a mushroom shape, a T shape, and a double J shape (a shape bonded back to back of a J shape), but may have any shape. Obviously, an adhesive material layer can also be provided as an engagement portion of the fastening tape 13.

In addition to various nonwoven fabrics such as a spun-bonded nonwoven fabric, an air-through nonwoven fabric, and a spunlace nonwoven fabric, a plastic film, a polyethylene laminated nonwoven fabric, paper, or a composite material thereof can be used as the sheet base material forming from the tape attaching portion to the tape main unit section.

(Target Sheet)

It is preferable to provide a target sheet 12T having a target for facilitating engagement at the engagement portion of each fastening tape 13 in the ventral side portion F. In the case where the engagement portion is the hook member 13A, the target sheet 12T can be used having a large number of loops made of threads to which engagement projections of the hook member are tangled, are provided on a surface of the sheet base member made of a plastic film or a nonwoven fabric. Further, in the case of an adhesive layer, it is possible to use a sheet base material made of a plastic film having a smooth surface with high adhesiveness and subjected to a release treatment. In the case where the engagement portion of the fastening tape 13 in the ventral side portion F is made of a nonwoven fabric, for example, when the outer sheet 12 in the illustrated embodiment is made of a nonwoven fabric, and the engagement portion of the fastening tape 13 is the hook member 13A, the target sheet 12T may be omitted, and the hook member 13A can be entangled and engaged with the nonwoven fabric of the outer sheet 12. In this case, the target sheet 12T may be provided between the outer sheet 12 and the liquid impervious sheet 11.

(Absorber)

The absorber 50 is a part that absorbs and retains the liquid content of excrement. The absorber 50 can be adhered to the components on at least one of the front surface side and back surfaces side via an adhesive such as a hot melt adhesive.

Figure 7A:
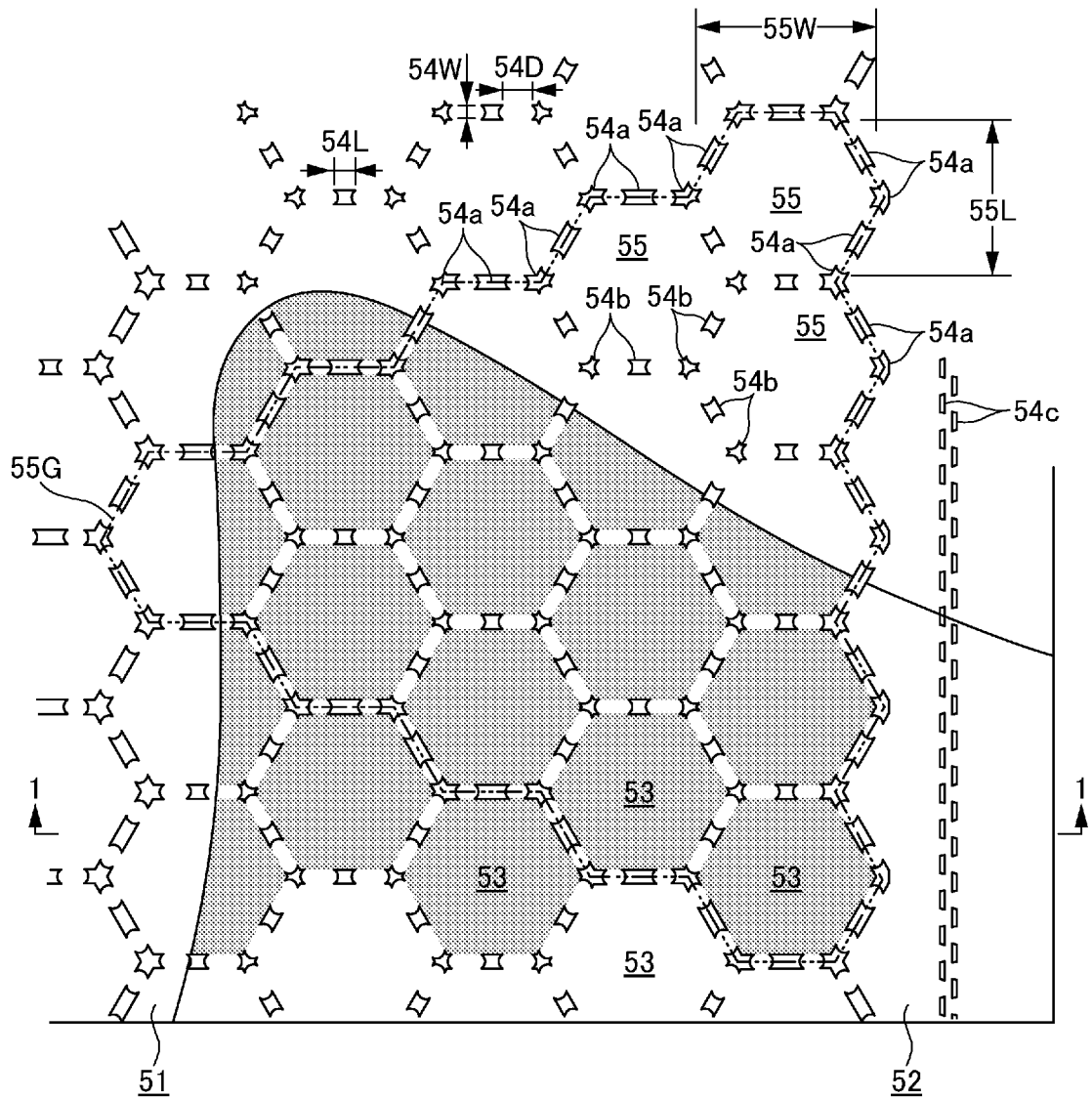
FIG. 7A is a fragmentary plan view of a main part of an absorber.
Figure 7B:
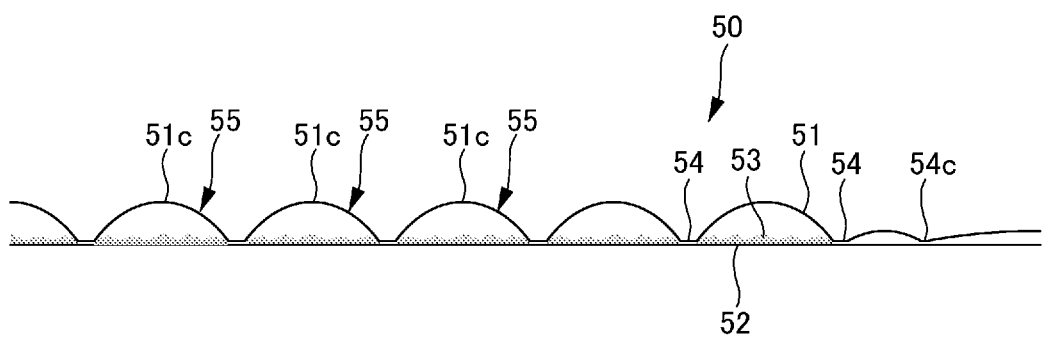
FIG. 7B is a cross-sectional view thereof taken along line 1-1.

As illustrated in the enlarged view of FIGS. 7A and 7B, the absorber 50 is surrounded by the front surface side sheet 51, the back surface side sheet 52 disposed on the back surface side of the front surface side sheet 51, and the bonded portions 54 of the front surface side sheet 51 and the back surface side sheet 52, and also the absorber 50 is a cell absorber 50 including a cell (small chamber) 55, in which the front surface side sheet 51 and the back surface side sheet 52 are not bonded, and the superabsorbent polymer particles 53 contained in the cell 55. In this way, by distributing and retaining the superabsorbent polymer particles 53 in a large number of cells 55 surrounded by the bonded portions 54, the uneven distribution of the superabsorbent polymer particles 53 in the absorber 50 can be prevented. The cell absorber 50 can be wrapped with a wrapping sheet (not shown). In this case, one wrapping sheet can be used for wrapping the absorber in a cylindrical shape so as to surround the front and back surfaces and both side surfaces of the absorber 50 and two wrapping sheets can be also used for wrapping the absorber so as to sandwich the same from both the front surface side and the back surface side. As the wrapping sheet, a tissue paper, particularly a crepe paper, a nonwoven fabric, a polyethylene laminated nonwoven fabric, a sheet with small holes, and the like can be used. However, it is desirable that the wrapping sheet be a sheet through which superabsorbent polymer particles do not pass. When a nonwoven fabric is used for a wrapping sheet, a hydrophilic SMS nonwoven fabric (SMS, SSMMS, etc.) is particularly suitable, and polypropylene, and polyethylene/polypropylene composite material can be used as a material. The basis weight is preferably 5 to 40 g/m.sup.2, particularly preferably 10 to 30 g/m.sup.2. When the cell absorber 50 is wrapped with a wrapping sheet, pulp fibers can be accumulated on one side of the front and back sides of the cell absorber, and these can be wrapped with a wrapping sheet collectively.

The front surface side sheet 51 may be a liquid-pervious material or a liquid impervious material, but preferably it is a liquid-pervious material when it is positioned on the top sheet 30 side as indicated in the illustrated embodiment. Similarly to the top sheet 30, a porous or non-porous nonwoven fabric or a porous plastic sheet can be used for the front surface side sheet 51. In the case of using a nonwoven fabric for the front surface side sheet 51, examples of the constituent fibers include synthetic fibers (including not only single component fibers but also conjugate fibers) such as olefin type such as polyethylene or polypropylene, polyester type, and polyamide type, regenerated fibers such as rayon and cupra, and natural fibers such as cotton, but it can be selected without limitation, and it is preferable to use a thermoplastic resin fiber because of excellent thermal processability. The fiber bonding method of the nonwoven fabric is not particularly limited, but to prevent the superabsorbent polymer particles 53 from falling off through the sheet, it is preferable to use a bonding method which increases fiber density, such as a spun bond method, a melt blown method, and a needle punch method. In the case of using a porous plastic sheet, its pore diameter is preferably smaller than the outer shape of the superabsorbent polymer particle 53 to prevent the superabsorbent polymer particle 53 from falling off through the sheet. When the material of the front surface side sheet 51 is hydrophobic, a hydrophilic agent can also be contained.

To facilitate the arrangement of the superabsorbent polymer particles 53 in the manufacturing and to secure the volume after the swelling due to the absorption, in the portion forming each cell 55 in the front surface side sheet 51, a recess 51c recessed from the back surface side to the front surface side is preferably formed.

The back surface side sheet 52 may be made of the same material as the front surface side sheet 51, but in the case where the front surface side sheet 51 is composed of a liquid pervious material, a liquid impervious material can be used for the back surface side sheet 52. The liquid impervious material usable for the back surface side sheet 52 can be appropriately selected and used from the materials described in the section of the liquid impervious sheet 11. Although not illustrated, the front surface side sheet 51 and the back surface side sheet 52 may be one side layer and another side layer in which one sheet of material is folded in two.

The superabsorbent polymer particles 53 may not be fixed to the front surface side sheet 51 and the back surface side sheet 52 and may be freely movable, but may also be bonded or adhered to the front surface side sheet 51 and the back surface side sheet 52. Also, the superabsorbent polymer particles 53 may be agglomerated to some extent.

As the superabsorbent polymer particles 53, those used for this type of absorbent articles can be used on an as is basis. The particle diameter of the superabsorbent polymer particles is not particularly limited, but for example, when the particles are sieved (shaking for five minutes) using a standard sieve (JIS Z8801-1:2006) of 500.mu.m and the particles subjected to sieving with the 500.mu.m standard sieve are further sieved (shaking for five minutes) using the standard sieve (JIS Z8801-1: 2006) of 180.mu.m, preferably the proportion of the particles remaining on the 500 .mu.m standard sieve is 30% by weight or less, and the proportion of the particles remaining on the 180.mu.m standard sieve is 60% by weight or more.

The material of the superabsorbent polymer particles 53 can be used without particular limitation, but the material having the water absorption capacity of 40 g/g or more is suitable. Examples of the superabsorbent polymer particles 53 include starch-based, cellulose-based, and synthetic polymer-based, and starch-acrylic acid (salt) graft copolymers, saponified starch-acrylonitrile copolymers, sodium carboxymethyl cellulose crosslinked products, acrylic acid (salt) polymers and the like. As the shape of the superabsorbent polymer particles 53, the shape of particulate materials which are usually used is suitable, but other shapes can also be used.

The superabsorbent polymer particles 53 having a water absorption rate of 70 seconds or less, particularly 40 seconds or less, are suitably used. If the water absorption rate is too slow, so-called returning, in which the liquid fed into the absorber 50 returns to the outside of the absorber 50, is likely to occur.

The superabsorbent polymer particles 53 having the gel strength of 1,000 Pa or more are preferably used. Thereby, even when the absorber 50 is bulky, it is possible to effectively suppress stickiness after liquid absorption.

The basis weight of the superabsorbent polymer particles 53 can be appropriately determined according to the absorption amount required for the use of the absorber 50. Therefore, although it cannot be said unconditionally, the basis weight can be 50 to 350 g/m$^2$. When the basis weight of the polymer is less than 50 g/m$^2$, it is difficult to secure the absorption amount. When it exceeds 350 g/m$^2$, the effect is saturated.

The planar shape of the cell 55 can be determined as appropriate, and it may be circular, elliptical, or the like, but the shape is preferably a polygon to provide a denser arrangement. In addition to arranging the cells 55 having the same shape and the same size, the cells 55 may be arranged by combining multiple types of cells varying at least one of the shape and size.

Figure 8A:
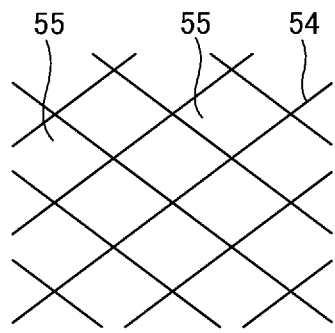
FIGS. 8A-E illustrate schematic plan views illustrating various arrangement examples of cells.
Figure 8B:
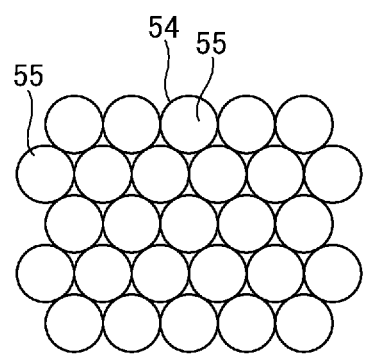
Figure 8C:
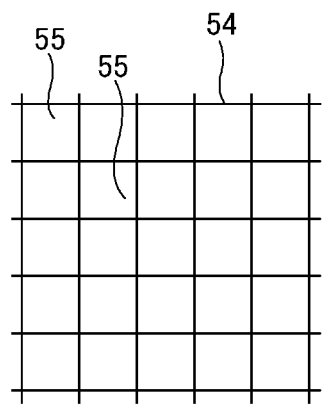
Figure 8D:
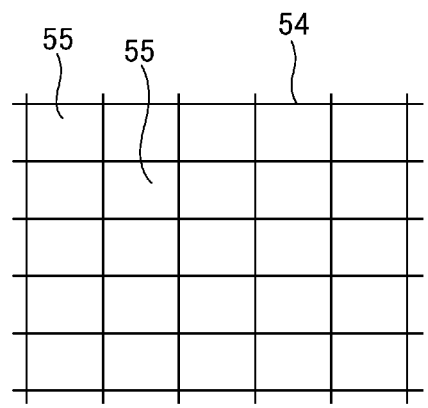
Figure 8E:
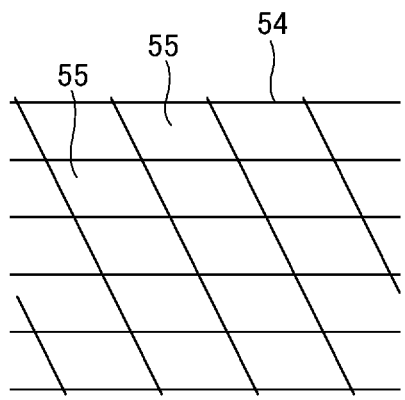

Although the planar arrangement of the cells 55 (that is, also the collecting portions of the superabsorbent polymer particles 53) can be appropriately determined, a regularly repeated plane arrangement is preferred. In addition to the regularly repeated plane arrangement, such as an oblique lattice shape as illustrated in FIG. 8A, a hexagonal lattice shape (also referred to as a staggered shape) as illustrated in FIG. 8B, a square lattice shape as illustrated in FIG. 8C, a rectangular lattice shape as illustrated in FIG. 8D, and a parallel lattice shape as illustrated in FIG. 8E (two groups of many parallel oblique direction rows are provided so as to cross each other) (including those inclined at an angle of less than 90.degree. with respect to the stretchable direction), a group of the cells 55 (the group may be regularly or irregularly arranged, and may be a pattern or a letter shape) can be regularly repeated.

The size of each cell 55 can be appropriately determined, and for example, the length 55L in the front-back direction LD can be about 8 to 30 mm, and the length 55W in the width direction WD can be about 10 to 50 mm It is desirable that the bonded portion 54 for bonding the front surface side sheet 51 and the back surface side sheet 52 be bonded by welding the front surface side sheet 51 and the back surface side sheet 52 like ultrasonic welding or heat sealing, but it may be bonded with a hot melt adhesive.

As long as each cell 55 is surrounded by one or a plurality of bonded portions 54 for bonding the front surface side sheet 51 and the back surface side sheet 52, the bonded portions 54 may be arranged in a dotted line shape (intermittently in a direction surrounding each cell 55) as indicated in the illustrated embodiment and the bonded portion also may be formed in a continuous linear shape. In the case of intermittently forming the bonded portions 54, the superabsorbent polymer particles 53 are not present between the bonded portions 54 in the direction surrounding the cell 55, or even if the superabsorbent polymer particles 53 are present, less superabsorbent polymer particles than those in the cell 55 are included.

The size of the bonded portion 54 for bonding the front surface side sheet 51 and the back surface side sheet 52 can be appropriately determined, and for example, the line width (dimension in the direction orthogonal to the direction surrounding the cell 55) 54W can be about 0.6 to 8.0 mm. In the case of forming the bonded portions 54 in a dotted line shape (intermittent in the direction surrounding the cell 55), it is preferable that the length 54L of the bonded portion 54 in the direction surrounding the cell 55 is about 0.6 to 8.0 mm, and the point interval 54D is about 0.8 to 10.0 mm. In particular, in the case of the strong bonded portion 54a, it is preferable that the line width 54W is about 1.0 to 4.0 mm, the length 54L of the bonded portion 54 is about 1.5 to 4.0 mm, and the point interval 54D is about 0.8 to 2.5 mm. In the case of the weak bonded portion 54b, it is preferable that the line width 54W is about 0.6 to 3.5 mm, the length 54L of the bonded portion 54 is about 0.6 to 2.5 mm, and the point interval 54D is about 1.0 to 4.0 mm.

The width of the bonded portion 54 in the case where the bonded portion 54 is formed in a continuous linear shape, and the line width 54W in the case where the bonded portions 54 are formed in a dotted line shape are constant in the direction surrounding the cell 55 and also can be changed. In addition, in the case where the bonded portions 54 are formed in a dotted line shape, the shape of each bonded portion 54 can be appropriately determined, and all of the bonded portions have the same shape, or the bonded portions may have different shapes depending on their positions. In particular, when each cell 55 has a polygonal shape, it is preferable to provide each bonded portion 54 at the intermediate position of each side of the polygon. Further, it is preferable to provide each strong bonded portion 54a at a position of each vertex, but it is preferable not to provide the weak bonded portion 54b at the position of each vertex so that the weak bonded portion 54b can be peeled off easily, resulting in smooth coalescing of the cells 55. In the case where the bonded portion 54 is provided at the position of each vertex, it is desirable that the bonded portion 54 has a radial (star) shape protruding in the direction of each side.

When the superabsorbent polymer particles 53 in each cell 55 are swollen due to the absorption to fill the inside of the cell 55, the front surface side sheet 51 and the back surface side sheet 52 are strongly bonded at the bonded portions 54 such that the bonded portions 54 are not peeled off against the internal pressure. However, when the superabsorbent polymer particles 53 fill the inside of each cell 55, there is a possibility that the absorption amount and absorption rate are lowered due to inhibition by the swelling and so-called gel blocking. Therefore, it is preferable that, because of the swelling pressure due to the absorption by the superabsorbent polymer particles 53 in each cell 55, the bonded portions 54 surrounding the cell 55 are partly or totally peeled off, and the cell 55 coalesces with the adjacent cells 55 to form a larger cell 55. Such a function is realized, for example, by providing the weak bonded portions 54b with weakened bonding strength in appropriate places and by determining the type and amount of the superabsorbent polymer particles 53 disposed in each cell 55 such that the volume of the superabsorbent polymer particles 53 in the cell 55 upon the saturation absorption becomes sufficiently larger than the volume of the cell 55.

Figure 9:
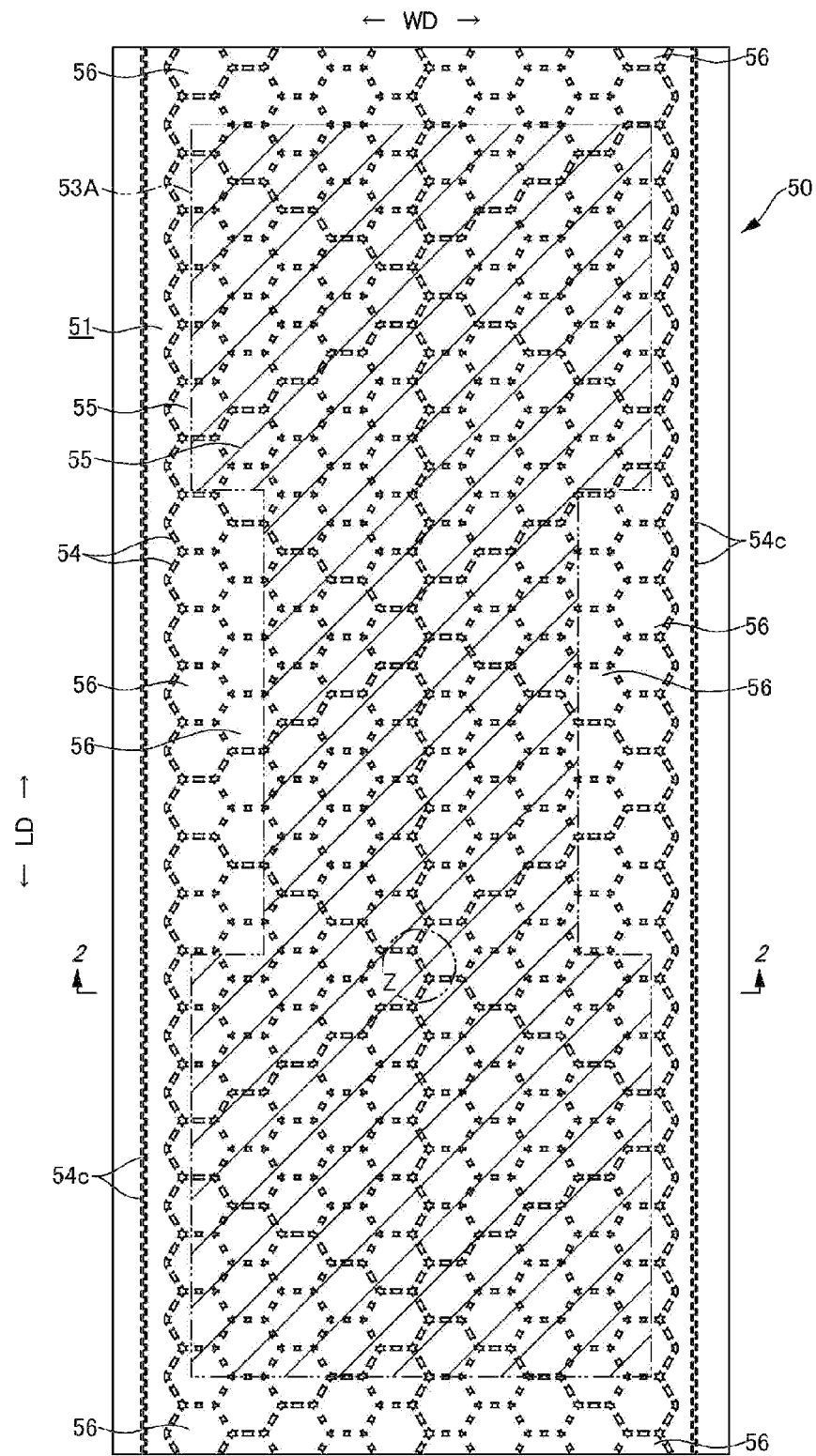
FIG. 9 is a plan view of the absorber.
Figure 10:
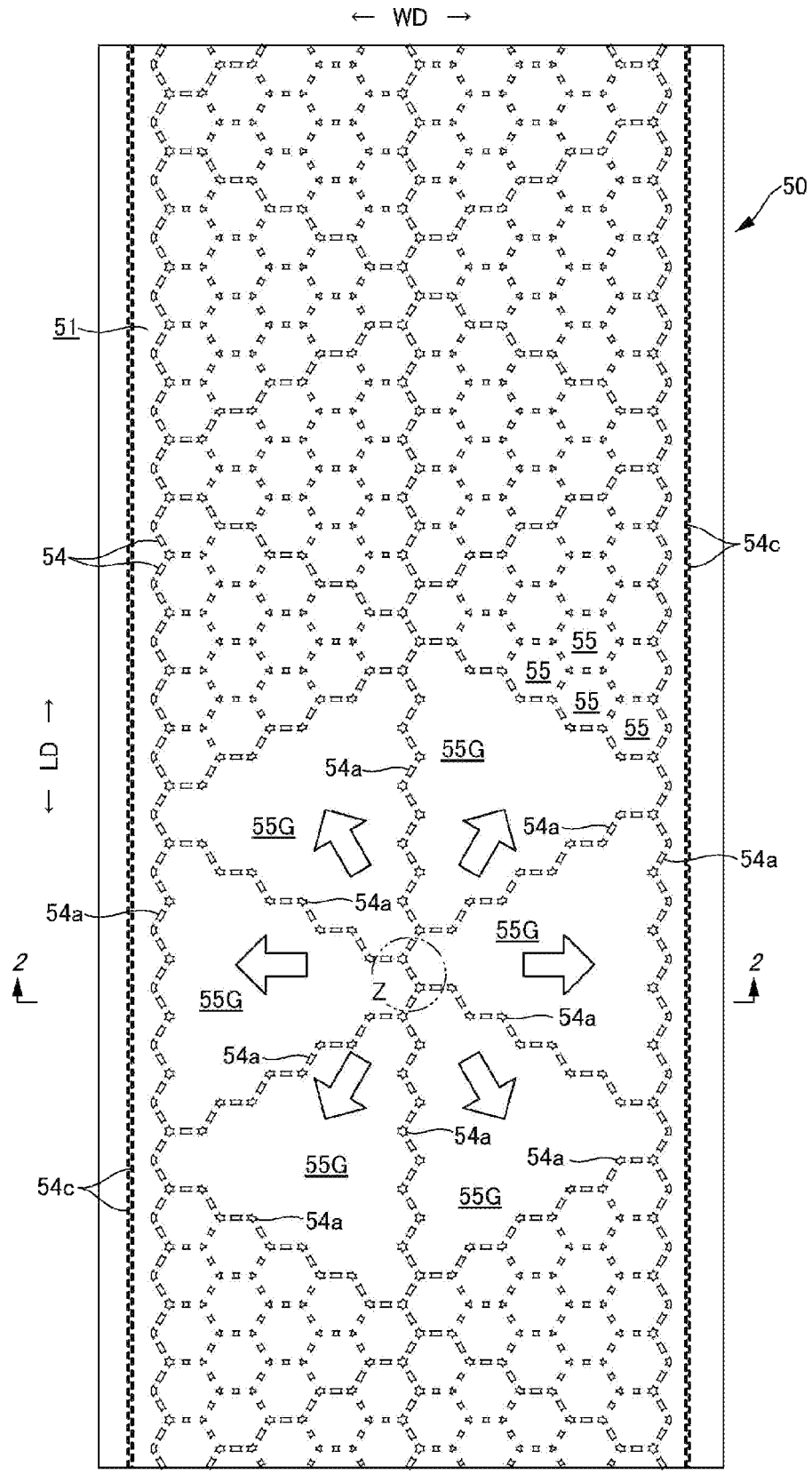
FIG. 10 is a plan view of the absorber.
Figure 11:
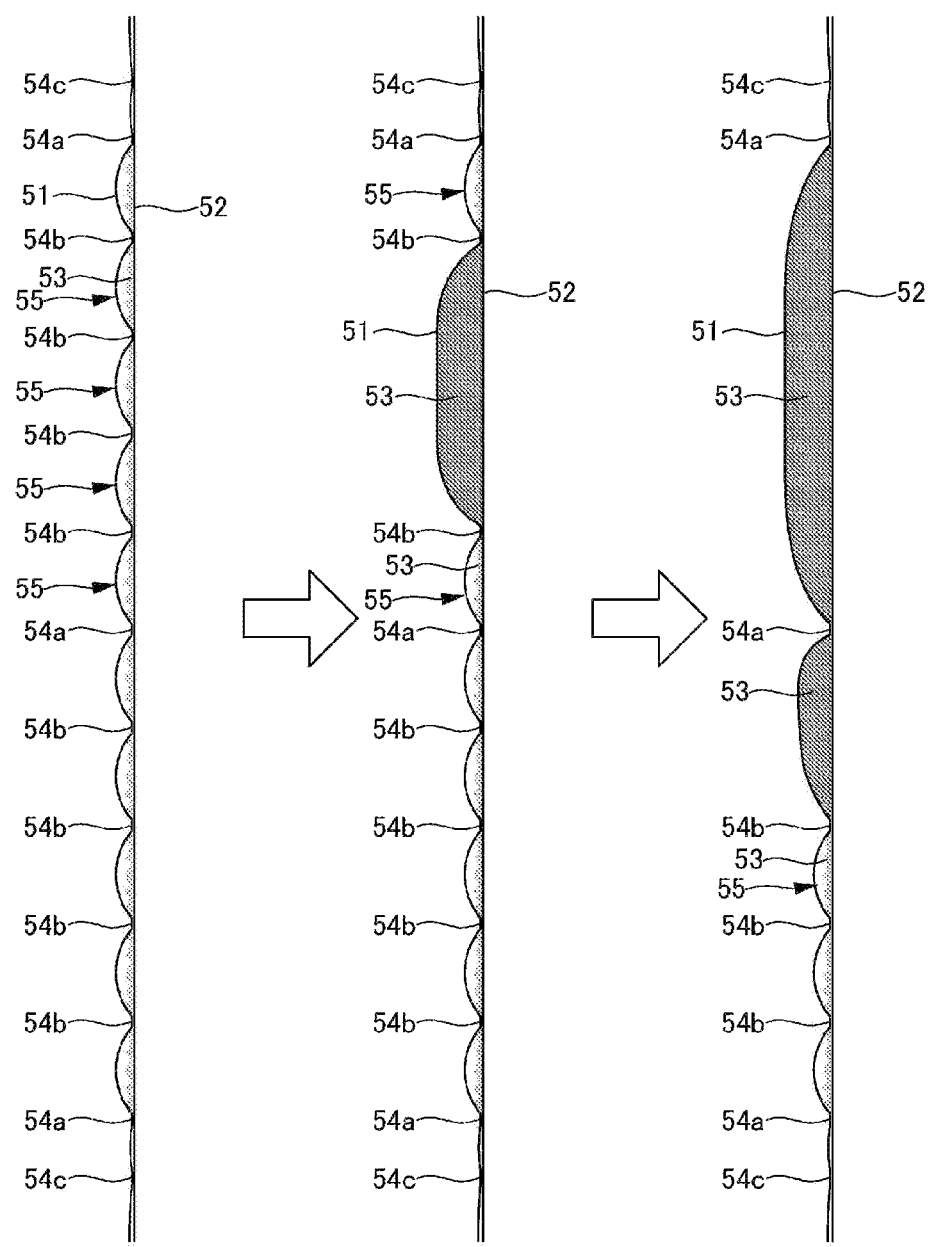
FIG. 11 is a cross-sectional view taken along the line 2-2 in FIGS. 9 and 10.

Although the bonding strength of the bonded portions 54 may be uniform over the entire absorber 50, as illustrated in FIGS. 7A and 7B, 9, and 10, one of the preferable embodiments is that the planar region of the absorber 50 is divided into a plurality of compartments 55G, the bonded portions 54 surrounding the group of the cells 55 of each compartment 55G are formed as strong bonded portions 54a having relatively high bonding strength, the bonded portions 54 located inside the compartment 55G are formed as weak bonded portions 54b having relatively low bonding strength, and the weak bonded portions 54b are peeled off in preference to the strong bonded portions 54a. In this case, all of the weak bonded portions 54b in the compartment 55G are peeled off by the swelling pressure due to the absorption by the superabsorbent polymer particles 53 in each cell 55 to form one cell 55 covering over the entire compartment 55G, subsequently, the strong bonded portions 54a surrounding the compartment 55G may be peeled off by the swelling pressure due to the absorption by the superabsorbent polymer particles 53 in the compartment 55G. Instead, if the strong bonded portions are not peeled off, the gelled material of the superabsorbent polymer particles 53 swollen due to the absorption is hardly moved and gathered to a low place such as a crotch portion, thus unsatisfactory fitting is not caused. For example, in the embodiment illustrated in FIG. 9, assuming that urine is excreted at the position of the reference sign Z, urine is diffused around the position as illustrated in FIG. 10, and the superabsorbent polymer particles 53 absorb the urine at respective positions. At this time, as illustrated in FIGS. 10 and 11, with regard to each cell 55 in which the swelling pressure of the superabsorbent polymer particles 53 is increased, the weak bonded portions 54b around the cell 55 cannot resist the swelling pressure and peels off and the cell 55 coalesces with the adjacent cells 55. This coalescence can proceed to reach the cells 55 having the strong bonded portions 54a therearound as long as the weak bonded portions 54b can be peeled off by the superabsorbent polymer particles 53 swollen due to the absorption. Such a function is realized, for example, by determining the type and amount of the superabsorbent polymer particles 53 disposed in each cell 55 such that the volume of the superabsorbent polymer particles 53 in the cell 55 upon saturation absorption becomes sufficiently larger than the volume of each cell 55, and the volume of the superabsorbent polymer particles 53 in the compartment 55G upon saturation absorption becomes less than the volume of the cells 55 of the entire compartment 55G surrounded by the strong bonded portions 54a upon the coalescence.

Although the arrangement of the strong bonded portions 54a is not particularly limited, for example, as indicated in the illustrated embodiment, if the strong bonded portions 54a continue throughout a certain range in a specific direction, such as the front-back direction LD, the width direction WD, and the oblique direction, the cells 55 on the both sides are swollen due to the absorption by the internal superabsorbent polymer particles 53, the strong bonded portions 54a are however not peeled off to the end. Therefore, after the absorption, the grooves with the bottom portions of the strong bonded portions 54a are formed along the specific directions, and the liquid diffusibility in the directions along the grooves is improved. In addition, if the strong bonded portions 54a continue in the width direction WD or in the oblique direction, it is possible to prevent the uneven distribution which would be caused by the movement of the gelled superabsorbent polymer particles 53 swollen due to the absorption as well as to improve the liquid diffusibility in the directions. Further, if the bonded portions positioned on the outermost side in the width direction WD are peeled off, there is a possibility that the superabsorbent polymer particles 53 or the gelled superabsorbent polymer particles 53 leak out laterally from the absorber 50, and it is therefore desirable that such bonded portions are the strong bonded portions 54a. From the same viewpoint, it is preferable that the front surface side sheet 51 and the back surface side sheet 52 are extended laterally in the width direction WD to some extent beyond the region where the cells 55 are formed, and the edge bonded portions 54c are provided in the extended portions for the reinforcement.

The difference in bonding strength may be easily made by changing the area of each bonded portion 54 but is not limited thereto. For example, in the case of forming the bonded portion 54 with a hot melt adhesive, a method in which the type of a hot melt adhesive is varied depending on the sites can be used.

As illustrated in FIG. 9, it is also possible to provide the empty cells 56 which do not contain the superabsorbent polymer particles 53 or which contain a smaller amount of the superabsorbent polymer particles 53 than other cells even if the cells contain them. In FIG. 9, an area 53A having a pattern of hatched lines indicates a region for containing the superabsorbent polymer particles 53. Since this region is based on assumption of the shape of a region in which the superabsorbent polymer particles 53 are dispersed in the manufacturing, there are portions which are not covered by the pattern of the hatched lines in the cells 55 in the peripheral edge. Actually, in the case where the superabsorbent polymer particles 53 can move in each cell 55, the positions of the superabsorbent polymer particles 53 in the cell 55 are not fixed in a state of the product, and the superabsorbent polymer particles 53 can be distributed throughout the cells 55 in the same manner as in the state illustrated in FIGS. 7A and 7B. The amount of the superabsorbent polymer particles 53 contained in the empty cell 56 is preferably ½ or less, particularly ¹⁄₁₀ or less, of the other cells in terms of weight ratio, and it is particularly preferable that the superabsorbent polymer particles 53 are not contained at all in the empty cell. For example, since the front end and the back end of the absorber 50 are formed by cutting into the individual absorbers 50 in the manufacturing, if the superabsorbent polymer particles 53 are contained in portions where the cutting is performed, the life of a blade of a cutting device may be shortened. Therefore, it is desirable that at least the cells 55 located at the positions through which the front and back ends of the absorber 50 pass be the empty cells 56. Further, in the absorber 50 obtained by mixing superabsorbent polymer particles 53 with a hydrophilic short fiber such as fluff pulp, and being accumulated in a cotton form, generally, the intermediate portion in the front-back direction LD is formed in a narrow shape so as to be along the legs. However, also in the cell absorber 50, by setting, the cells 55 on the both sides in the intermediate portion in the front-back direction LD, as the empty cells 56, the intermediate portion in the front-back direction LD will be less swollen even after the absorption. Therefore, the absorber 50 has a shape that fits around the legs even after the absorption.

In the case of manufacturing the absorber 50, since it is difficult to accurately distribute a predetermined amount of the superabsorbent polymer particles 53 to the individual cells 55, it is preferable that the superabsorbent polymer particles 53 are uniformly dispersed throughout the entire region for containing the superabsorbent polymer particles 53 (the region excluding the portions to be the empty cells 56) on the front surface side sheet 51 or the back surface side sheet 52, and then the bonded portions 54 are formed to bond the front surface side sheet 51 and the back surface side sheet 52 as one unit and to confine the superabsorbent polymer particles 53 in each cell 55. In this case, particularly with respect to the peripheral cells 55 positioned in the peripheral edge of the region for containing the superabsorbent polymer particles 53, it is difficult to disperse the superabsorbent polymer particles 53 in an accurate shape matching with the peripheral edge of the cells 55. Therefore, as can be seen from the shape of the dispersing region 53A which is defined for dispersing the superabsorbent polymer particles 53 and indicated by the pattern of hatched lines in FIG. 9, it is desirable to disperse the superabsorbent polymer particles 53 such that the peripheral edge of the region 53A for the dispersion passes through the middle of the peripheral cells 55. In this case, the amount of the superabsorbent polymer particles 53 contained in the peripheral cells 55 is less than the amount of the same contained in the cells 55 positioned inside the peripheral cells 55, and in the case where the cells 55 are further provided outside the peripheral cells 55, these outer cells 55 become the empty cells 56 which do not substantially contain the superabsorbent polymer particles 53.

In the above example, only the superabsorbent polymer particles 53 are contained in the cells 55, but it is also possible to contain the superabsorbent polymer particles 53 together with particulate materials other than the superabsorbent polymer particles 53, such as deodorant particles.

<Manufacturing of Absorber>

The above-described cell absorber 50 is manufactured by conveying a continuous belt-shaped first sheet along a continuous direction, sequentially forming a large number of recesses on the first sheet in this conveying process at intervals in the CD while the first sheet is conveyed, feeding particulate materials including superabsorbent polymer particles to the recesses of the first sheet on the downstream side of the recess forming position, overlapping a belt-shaped second sheet continuous in the MD on the first sheet on the downstream side of the feeding position of the particulate materials, bonding portions among the recesses of the first sheet and the second sheet on the downstream side of the position where the second sheet is overlapped, sequentially forming a continuous series of the absorbers in which a large number of cells containing particulate materials are arranged, and cutting a continuous series of the absorbers into individual absorbers at intervals in the MD. Although it is preferable that the first sheet is the front surface side sheet of the above-described cell absorber 50 and the second sheet is the back surface side sheet, those may be set opposite.

Figure 12:
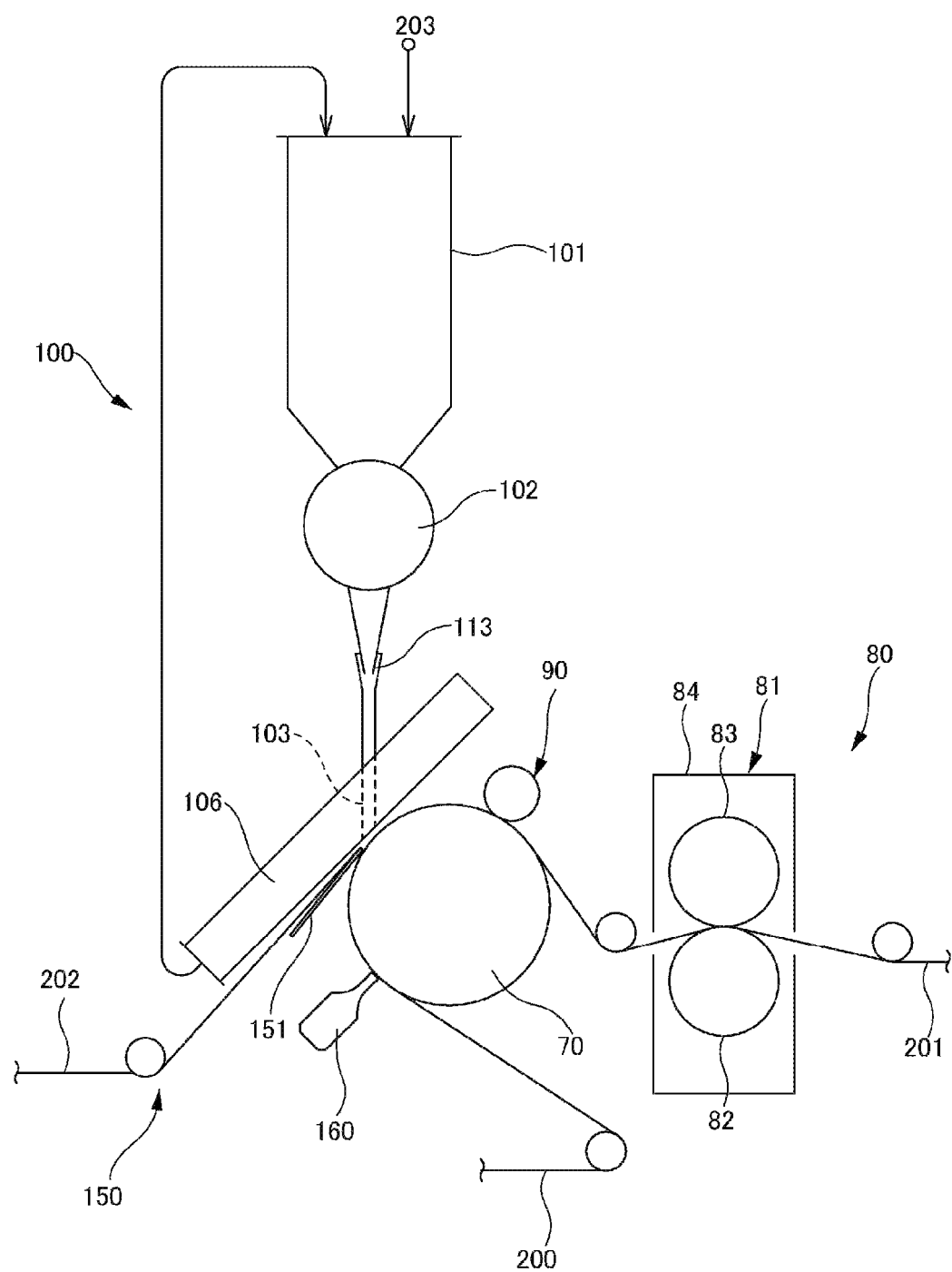
FIG. 12 is a flow diagram of facilities for manufacturing the absorber.

FIG. 12 illustrates a specific example of a device for manufacturing the cell absorber. This manufacturing device is based on an anvil roll 70 which is driven to rotate about a lateral rotating shaft. Within the rotation direction range of the upper half of the anvil roll 70, in the order from the upstream side in the rotation direction, the first sheet feeding unit 80, a recess forming unit 90, a particulate material feeding device 100, and a second sheet feeding unit 150 are provided. In addition, a welding unit 160 is provided on the downstream side in the rotation direction of the feeding unit of the second sheet.

Figure 13:
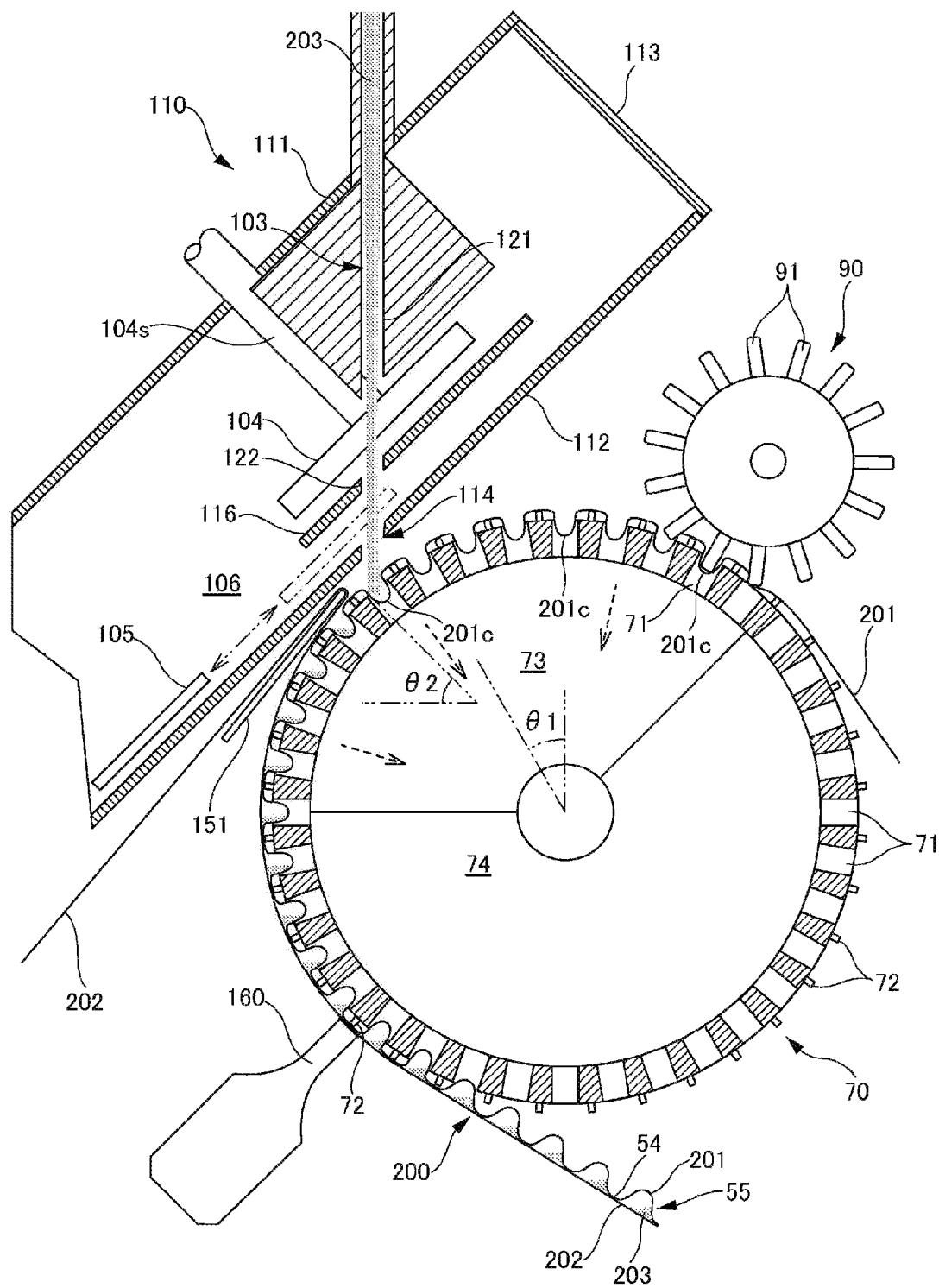
FIG. 13 is a cross-sectional view of a main part schematically illustrating the facilities for manufacturing the absorber.
Figure 14A:
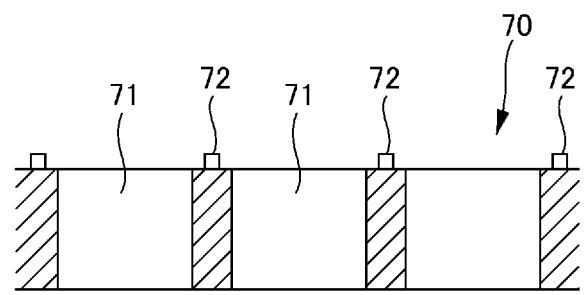
FIG. 14A is a cross-sectional view of a main part of an anvil roll.
Figure 14B:
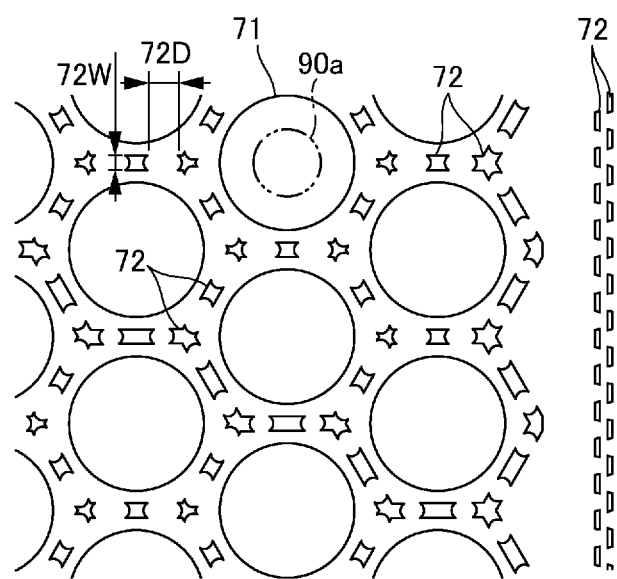
FIG. 14B is a plan view of an anvil roll in which the outer peripheral surface is spread in a plane.

As also illustrated in FIGS. 13, 14A and 14B, the anvil roll 70 has a large number of concaves 71 arranged at intervals on the outer peripheral surface, and for each concave 71, projections 72 provided so as to surround the concave 71 in a portion among the concaves 71. The concave 71 on the outer peripheral surface of the anvil roll 70 communicates with the inner space partitioned into a suction compartment 73 and a non-suction compartment 74 in the rotation direction. A suction device such as a suction fan (not illustrated) is connected to the suction compartment 73 in the inner space of the anvil roll 70, and the inside of the concave 71 can be sucked. In addition, neither a suction port nor a discharge port is formed in the portion among the concaves 71 on the outer peripheral surface of the anvil roll 70.

The first sheet feeding unit 80 feeds a continuous belt-shaped first sheet 201 made of a liquid pervious nonwoven fabric in the rotation direction of the anvil roll 70 along the outer peripheral surface of the anvil roll 70. The first sheet feeding unit 80 includes various devices such as a guide roll and a drive roll in a path from the material roll of the first sheet 201 (not illustrated) to the outer peripheral surface of the anvil roll 70.

Figure 15:
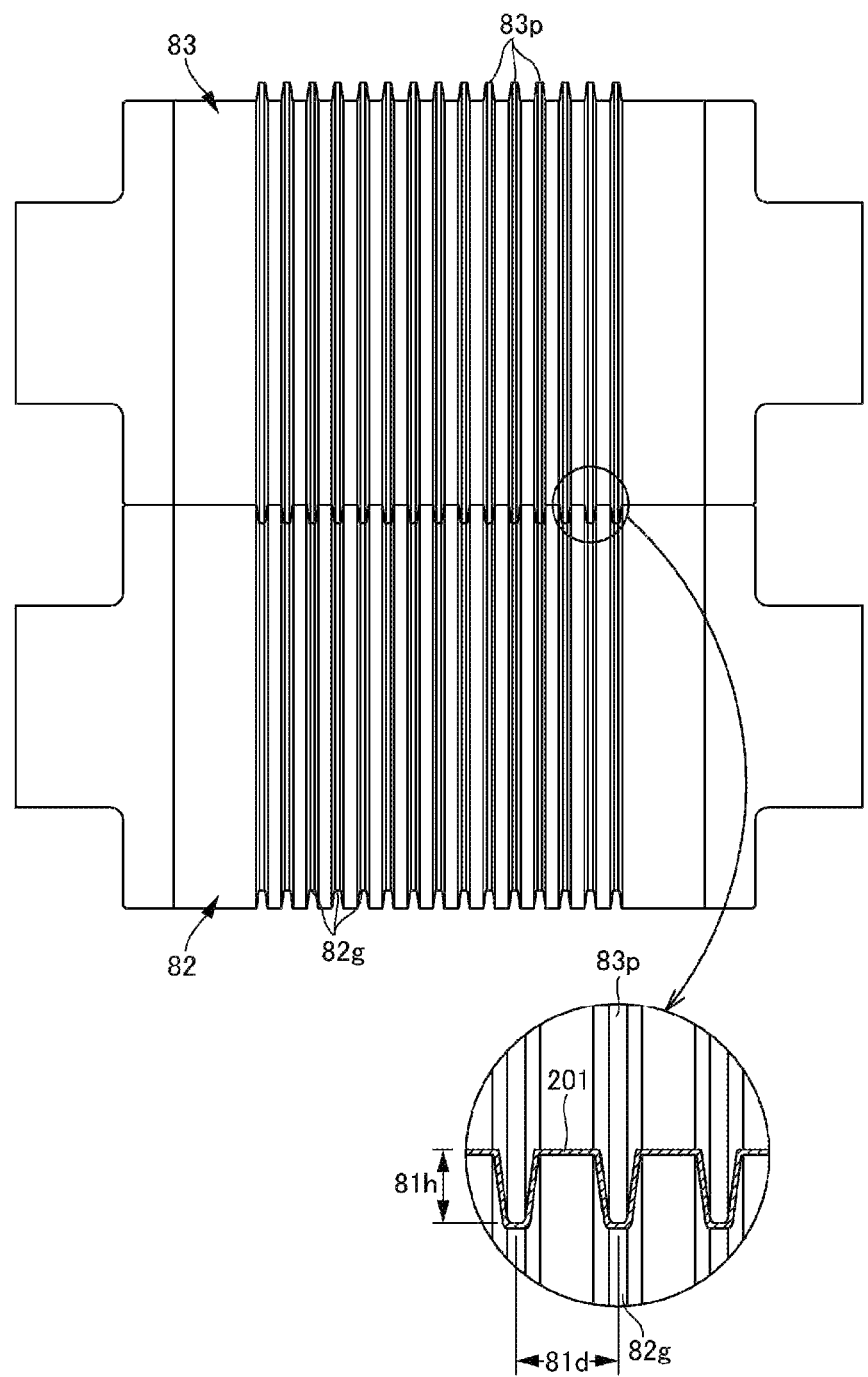
FIG. 15 is a front view of a corrugating device.

It is preferable that the first sheet feeding unit 80 includes a wave-forming device 81. As also illustrated in FIG. 15, the wave-forming device 81 includes a groove roll 82 having a large number of grooves 82g continuous in the roll circumferential direction and arranged in the roll length direction on the outer peripheral surface of the groove roll, and a convex roll 83 having a large number of convex portions 83p continuous in the roll circumferential direction and arranged in the roll length direction on the outer peripheral surface of the convex roll, while the groove roll 82 and the convex roll 83 are opposed to each other such that the grooves 82g and the continuous convex portions 83p are engaged with each other. Further, the wave-forming device includes a heating unit 84, where the groove roll 82 and the convex roll 83 pass, for heating the first sheet 201 to a melting temperature or lower. In the illustrated embodiment, the heating unit 84 is a heating box 84 which surrounds the convex roll 83 and the groove roll 82 and keeps the internal atmosphere at a predetermined temperature, but a heating unit for heating at least one of the groove roll 82 and the convex roll 83 may be used, or one heating unit for heating one of these rolls and the other heating unit for the other of these rolls may be combined. The temperature of the first sheet 201 in the wave-forming device 81 can be appropriately determined according to the type of the material, but it is preferable to set it at 40 to 100.degree. C. assuming the case of using a normal thermoplastic nonwoven fabric.

Figure 16A:
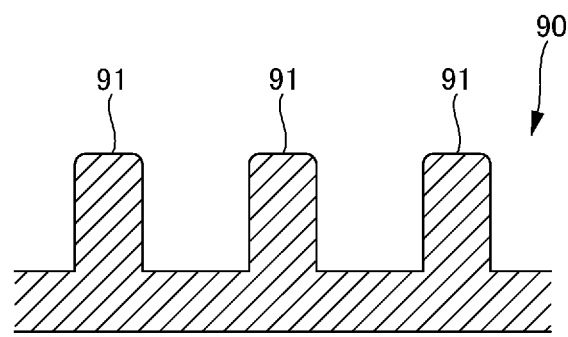
FIG. 16A is a cross-sectional view of a main part of a push-in roll.
Figure 16B:
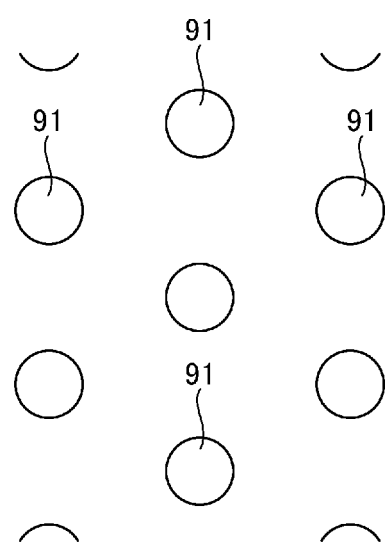
FIG. 16B is a plan view of the main part of a push-in roll in which the outer peripheral surface is spread in a plane.

By the recess forming unit 90, the first sheet 201 may be recessed to reach at least the second sheet 202 feeding unit by taking air in the concave 71 by the above-described suction unit. In the illustrated embodiment, as also illustrated in FIGS. 16A and 16B, as the recess forming unit 90, a push-in roll 90 is provided. The push-in roll 90 opposed to the anvil roll 70 has push-in pins 91 which enter the respective concaves 71 of the anvil roll 70. The push-in roll 90 forms receiving recesses 201c on the first sheet 201 by feeding the continuous belt-shaped first sheet 201 in the rotation direction of the anvil roll 70 between the anvil roll 70 and the push-in roll 90 and pushing the first sheet 201 into the concaves 71 by the push-in pins 91.

The particulate material feeding device 100 can be used without particular limitation as long as it drops and feeds the particulate materials 203 including the superabsorbent polymer particles 53. Here, the dropping and feeding includes free dropping under their own weights or more than that. As the particulate material feeding device 100, the following two types can be used: in one type, the particulate materials are fed continuously over the entire CD of a drop position and in another type, the particulate materials are fed intermittently at least a part in the CD of the drop position.

FIG. 13 and FIGS. 18 to 20 illustrate specific examples of the particulate material feeding device 100. The particulate material feeding device 100 includes the particulate material storage tank 101 for storing the particulate materials 203, the delivery device 102 for continuously delivering the particulate materials 203 stored in the particulate material storage tank 101, a chute 103 for dropping and transferring the particulate materials 203 delivered from the delivery device 102 and dropping and feeding the particulate materials 203 to a feeding position, blocking bodies 104 and 105 which intermittently enter blocking positions for blocking at least a part of particulate passage in a cross-sectional direction in the chute 103, from a non-blocking position, and a recovery path 106 branched from the chute 103 so as to discharge the particulate materials 203 blocked by the blocking bodies 104 and 105 to the outside of the chute 103.

In the illustrated embodiment, as the delivery device 102 for delivering the particulate materials 203 from the particulate material storage tank 101, a so-called rotary feeder 102 is connected to the lower end outlet of the particulate material storage tank 101, and by this rotary feeder 102, the particulate materials 203 stored in the particulate material storage tank 101 are continuously discharged and continuously and quantitatively fed to the chute 103. The delivery device 102 is not limited to the rotary feeder 102, and other known particulate material feeding devices 100 can be used. Further, the particulate materials may not be quantitatively supplied, for example, the feeding amount may be continuously or gradually changed.

As long as the chute 103 drops and transfers the particulate materials 203 to drop and feed the particulate materials 203 to the feeding position, a part or the whole of the particulate materials 203 may be dropped without coming into contact with the peripheral wall or may slide down on the peripheral wall. That is, the chute 103 may extend straight in the substantially vertical direction as indicated in the illustrated embodiment, and it may have a curved portion or a bent portion that draws an arc in part or in whole, unlike the illustrated embodiment. The passage position in the cross-sectional direction in the chute 103 may be changed continuously or gradually in the transfer direction, but in the case where intermittent feeding is performed only in a part in the CD, the passage position is desirably not changed in the CD or at least not reduced.

The blocking position of the blocking body 104, 105 is not particularly limited as long as it is a position blocking at least a part of the particulate passage in the sectional direction, but for example, the blocking position may be a position where the particulate passage in the middle in the CD in the chute 103 is not blocked, the particulate passage on the both sides is blocked, or a position where the particulate passage throughout the entire cross-sectional direction in the chute 103 is blocked. Alternatively, the first blocking body 104 may be provided at one of these blocking positions, and the second blocking body 105 may be provided on the other one.

As a drive mechanism for causing the blocking bodies 104 and 105 to intermittently enter the blocking position, the blocking bodies 104 and 105 can be linearly reciprocated with respect to the blocking positions by a crank mechanism or a fluid pressure cylinder, the blocking bodies 104 and 105 can be rotated about one point by a rotary drive source such as a motor to pass the rotational movement locus of the blocking bodies 104 and 105 through the blocking position, or the blocking bodies 104 and 105 can be rotated in parallel by the crank mechanism to pass the rotational movement locus of the blocking bodies 104 and 105 through the blocking position.

The recovery path 106 is a passage having an inlet in a direction in which the particulate materials 203 collide with the blocking bodies 104 and 105 and move, and the particulate materials 203 blocked by the blocking bodies 104 and 105 are discharged to the outside of the chute 103 by the moving force of a suction fan or the like or under their own weights. It is desirable that the blocked particulate materials 203 collected via the recovery path 106 be returned to the particulate material storage tank 101 for reuse as indicated in the illustrated embodiment, but the blocked particulate materials 203 may be temporarily stored in a storage tank or a storing bag for reuse, or may not be reused.

The particulate material feeding device 100 in the illustrated embodiment will be described in further detail. The chute 103, the blocking bodies 104 and 105, and the recovery path 106 are included in one box type unit. This box-type unit has a top plate 111, a bottom plate 112, and a side plate 113 covering the periphery of a space between the top plate 111 and the bottom plate 112. The box-type unit has a casing 110 arranged to be inclined with respect to the horizontal direction, a chute feeding port 114 provided on the upper side in the inclination direction of the top plate, a chute discharge port 115 provided on the lower side in the inclination direction of the chute feeding port 114, and chute main unit sections 121 and 122 for connecting these ports in the casing 110. A portion of the casing 110 on the lower side in the inclination direction of the chute main unit section 122 is a start point portion of the recovery path 106. The chute feeding port 114, the chute main unit sections 121 and 122, and the chute discharge port 115 have a substantially rectangular cross-sectional surface whose long side extends along the CD. The chute main unit sections 121 and 122 have a first passage 121 having an inlet provided below the chute feeding port 114 and extending in the substantially vertical direction from the inlet to a position above the first blocking position, and a second passage 122 having an inlet below the first blocking position and extending in the substantially vertical direction from the inlet to a position above the second blocking position on the chute discharge port 115.

The first passage 121 is a passage having a substantially rectangular cross-sectional surface formed with a pair of planes extending in the MD and a pair of planes extending in the CD. The second passage 122 is a through section having a substantially rectangular cross-sectional surface formed below the first blocking position in the partition plate 116 extending from the upper side to the lower side of the first blocking position in the inclination direction. The space of the first blocking position located between the outlet of the first passage 121 and the upper face of the partition plate 116 and the space of the second blocking position located between the outlet of the second passage 122 and the chute discharge port 115 open in the recovery path 106 on the obliquely lower side.

Figure 25:
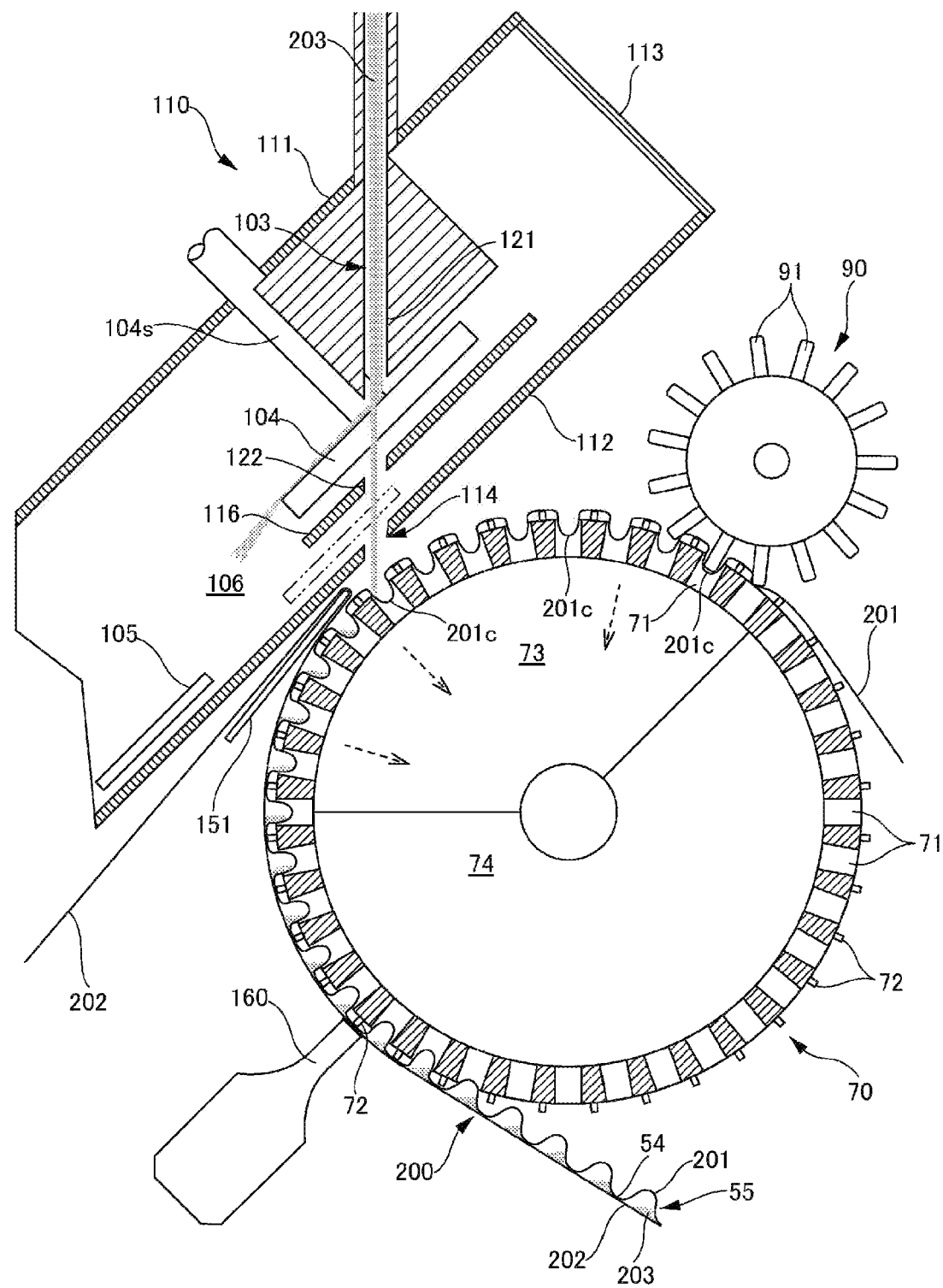
FIG. 25 is a cross-sectional view of a main part schematically illustrating facilities in a blocked state by a first blocking body.
Figure 26:
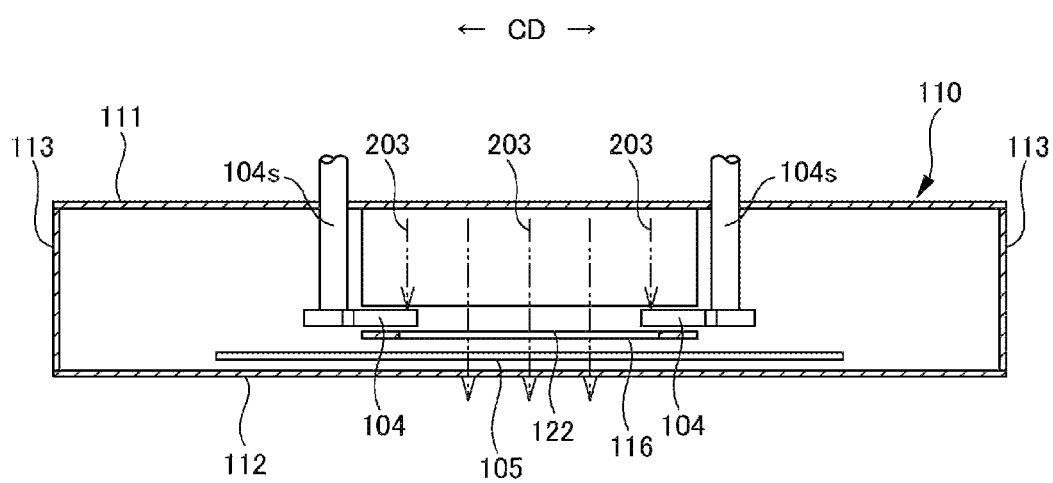
FIG. 26 is a cross-sectional view taken along line 4-4 of FIG. 19 and illustrates a blocked state by the first blocking body.

The first blocking body 104 in the illustrated embodiment comprises blade bodies (such as impellers) provided on the both sides in the CD in the first blocking position. Each black body is provided in a part of the rotation direction of a rotary shaft 104s extending in a direction intersecting the inclination direction on both sides in the CD of the first blocking position. By rotating the rotary shaft 104s by a rotary drive source (not illustrated), the first blocking body 104 repeats entering from the obliquely upper side and retracting from the obliquely lower side with respect to the both sides in the CD at the first blocking position. When the first blocking body 104 is in the retracted position, all of the particulate materials 203 dropping toward the inlet of the second passage 122 are allowed to pass through. However, when the particulate materials 203 pass through the first blocking position as indicated by rotation loca indicated by the two-dot chain lines in FIG. 19, the blocking body 104 does not block the particulate passage in the middle in the CD and blocks the particulate passage on the both sides thereof, as illustrated in FIGS. 25 and 26. Therefore, the space at the first blocking position also opens to the side such that the first blocking body 104 can enter and retract. The particulate materials 203 blocked by the first blocking body 104 move on the first blocking body 104 and the partition plate 116 and are introduced into the recovery path 106 on the lower side in the inclination direction.

Figure 27:
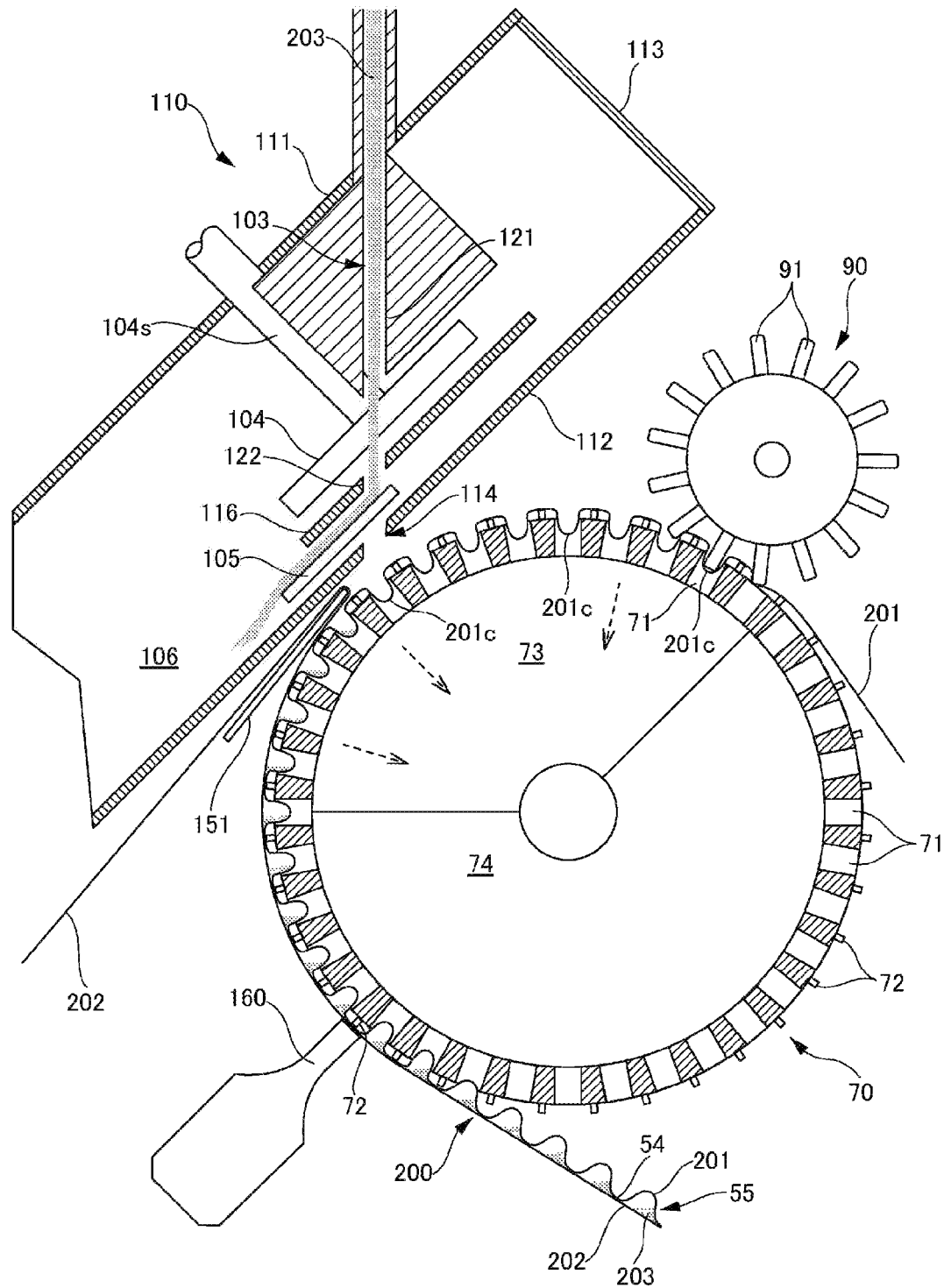
FIG. 27 is a cross-sectional view of a main part schematically illustrating the facilities in a blocked state by a second blocking body.

In addition, the second blocking body 105 in the illustrated embodiment is a blocking plate that is dimensioned to cover the entire chute discharge port 115 and that extends along the inclination direction. The second blocking body 105 is supported to be reciprocable in the inclination direction, and passes through the chute discharge port 115 in the process. When the second blocking body 105 is in the retracted position not covering the chute discharge port 115, all of the particulate materials 203 dropping toward the chute discharge port 115 are passed. When the second blocking body 105 passes through the blocking position on the chute discharge port 115, as indicated by two-dot chain lines in FIGS. 13 and 19 and illustrated in FIG. 27, all the particulate materials 203 dropping toward the chute discharge port 115 are blocked. The particulate materials 203 blocked by the second blocking body 105 move on the second blocking body 105 and the bottom plate 112 and are introduced into the recovery path 106 on the lower side in the inclination direction. The particulate materials 203 discharged from the chute discharge port 115 are sequentially dropped and fed onto the first sheet 201 wound around the outer peripheral surface of the anvil roll 70.

The second sheet feeding unit 150 disposed on the downstream side in the rotation direction of the particulate material feeding device 100 feeds a continuous belt-shaped second sheet 202 made of a liquid pervious nonwoven fabric in the rotation direction of the anvil roll 70 along the outer peripheral surface of the anvil roll 70. The second sheet feeding unit 150 includes various devices such as a guide roll and a drive roll in a path from the material roll (not illustrated) of the second sheet 202 to the outer peripheral surface of the anvil roll 70. In the illustrated embodiment, the guide plate 151, which approaches the vicinity of the outer peripheral surface of the anvil roll 70 in the tangential direction, is disposed, and the second sheet 202 passes over the guide plate 151, is folded back at its tip, and is fed in the rotation direction along the outer peripheral surface of the anvil roll 70. Therefore, the tip end of the guide plate 151 is an arcuate surface of a curved surface extending along the guiding direction of the second sheet 202.

Figure 17:
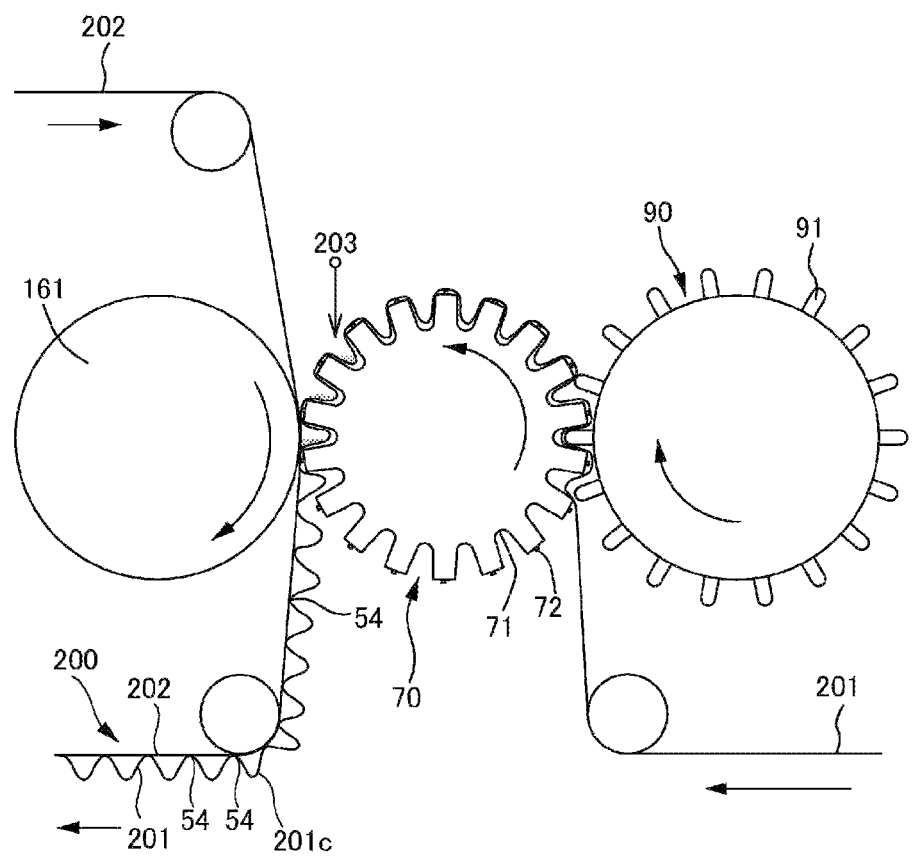
FIG. 17 is a cross-sectional view of a main part schematically illustrating other facilities for manufacturing an absorber.
Figure 18:
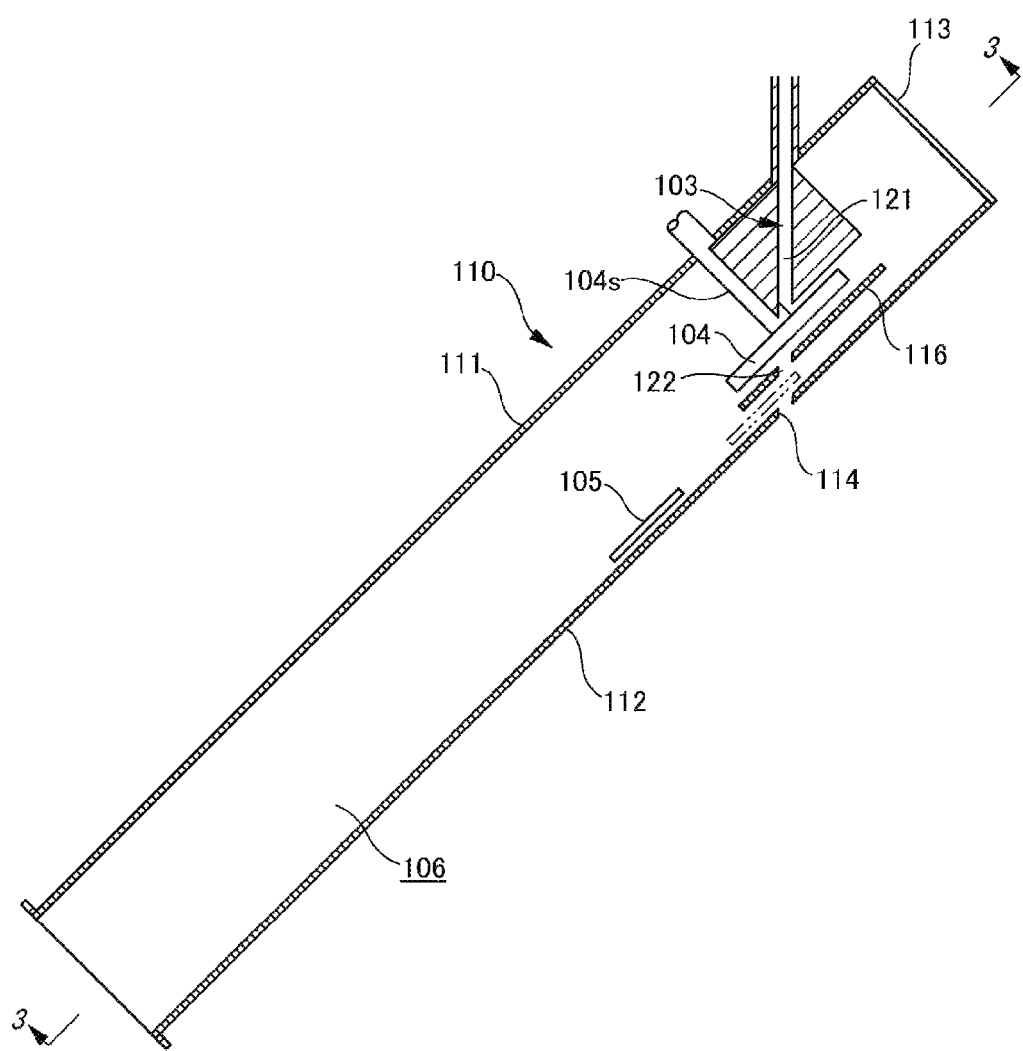
FIG. 18 is a longitudinal sectional view of a chute unit.
Figure 19:
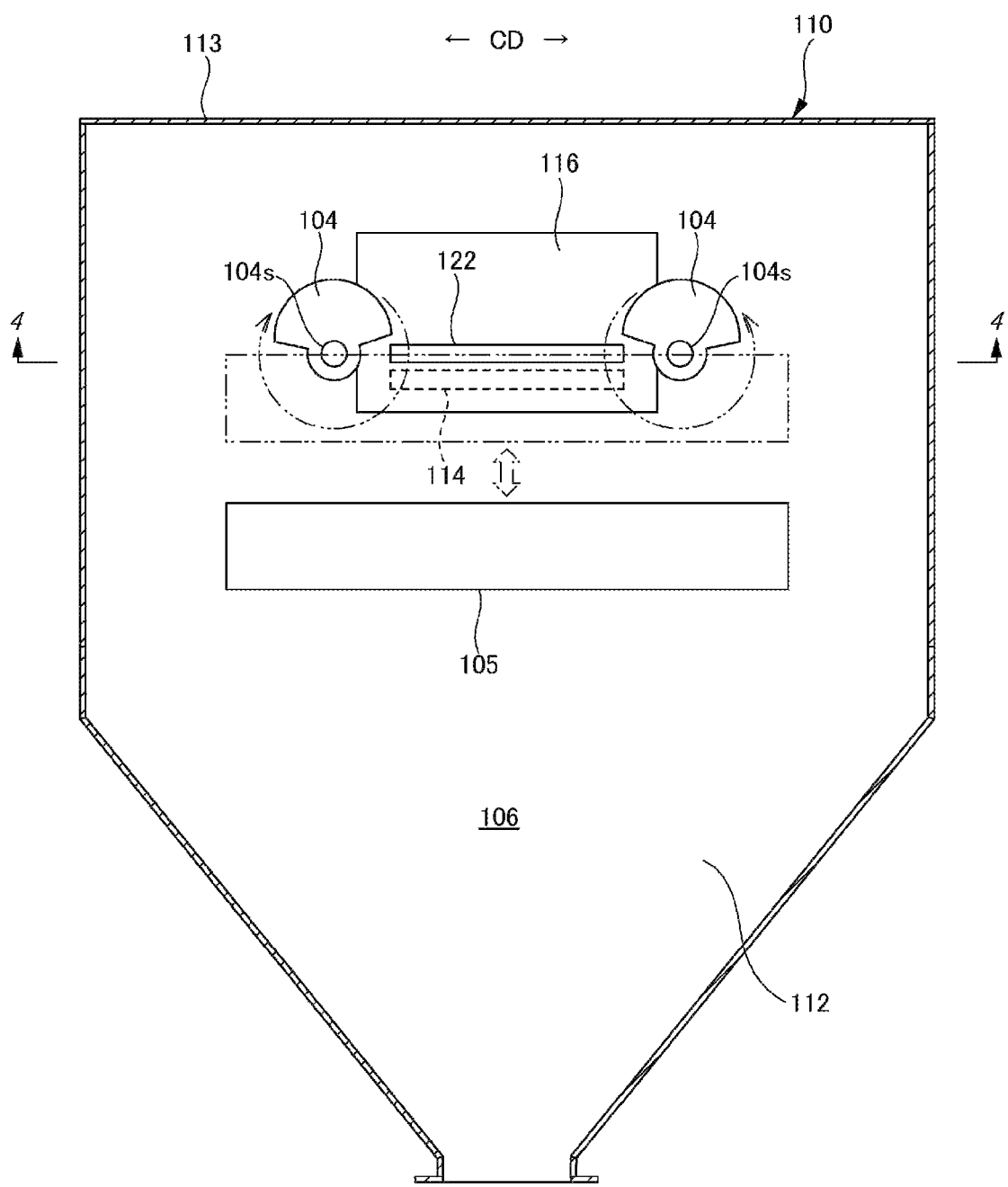
FIG. 19 is a cross-sectional view taken along line 3-3 of FIG. 18.
Figure 20:
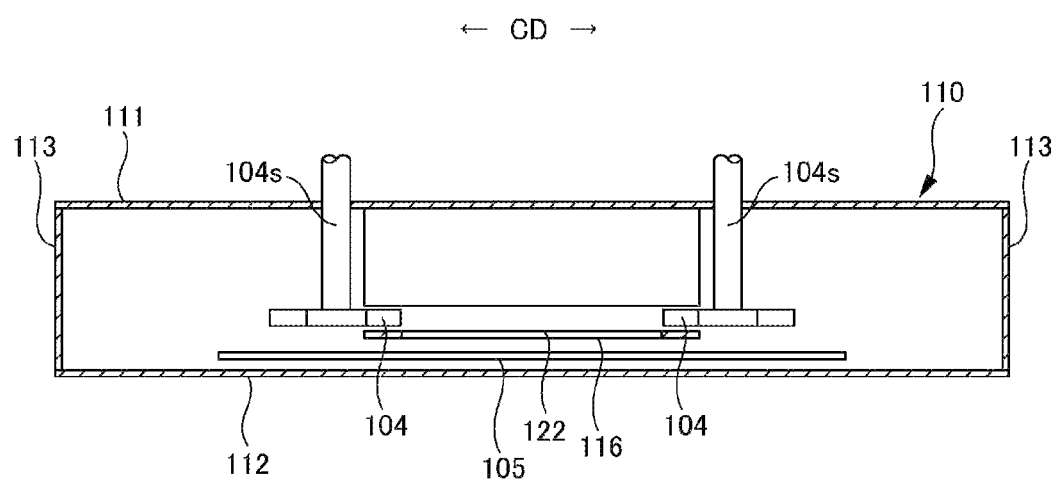
FIG. 20 is a cross-sectional view taken along line 4-4 of FIG. 19.

The welding unit 160 is not particularly limited as long as it welds the first sheet 201 and the second sheet 202. In addition to using the ultrasonic horn 160 of the ultrasonic welding apparatus as indicated in the embodiment of FIG. 12, a heating roll 161 may be used as indicated in the embodiment of FIG. 17.

Figure 21:
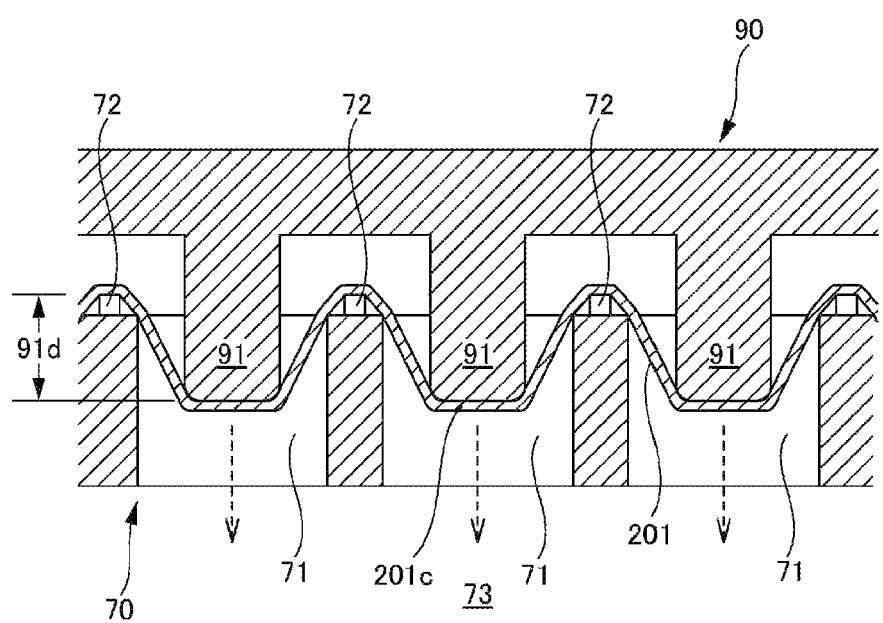
FIG. 21 is an enlarged cross-sectional view of a main part illustrating the recess forming step.
Figure 22:
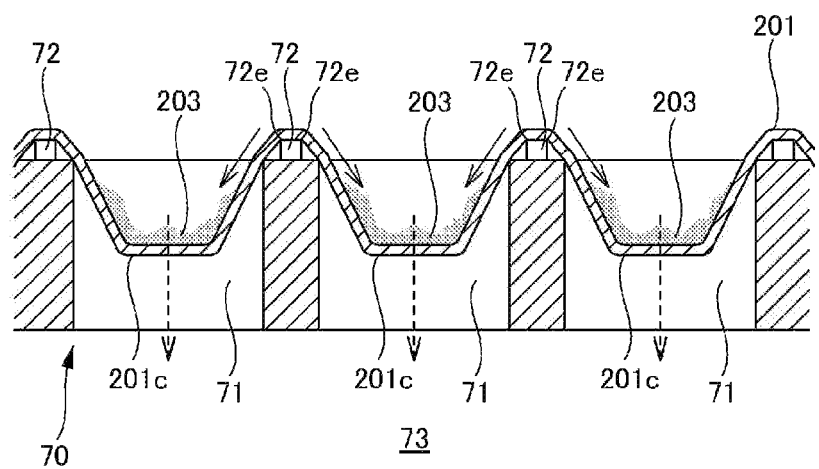
FIG. 22 is an enlarged cross-sectional view of a main part illustrating the step for feeding particulate materials.

In the manufacturing, as illustrated in FIGS. 13 and 21, the first sheet 201 is supplied to the anvil roll 70 by the first sheet feeding unit 80, and the receiving recesses 201c are sequentially formed in the first sheet 201 by the recess forming unit 90. In this case, by forming the receiving recesses 201c by a push-in roll as indicated in the illustrated embodiment, the receiving recesses 201c are formed more firmly as compared with the case where the receiving recesses 201c are formed by suction, and therefore it is preferable since the particulate materials 203 easily drop into each receiving recess 201c when the particulate materials are fed. Prior to the feeding of the first sheet 201 to the anvil roll 70, if the first sheet 201 is pretreated by the wave-forming device 81 as indicated in the illustrated embodiment, it is softened and becomes stretchable by the change in the fiber structure due to stretching of the first sheet 201. Therefore, in addition to further firmly forming the receiving recesses 201c in forming the receiving recesses 201c, the first sheet 201 is firmly sucked into the concaves 71 by suction such that the first sheet 201 becomes to have a surface shape easier to drop in the receiving recesses 201c, and thus it is preferable. To what extent the receiving recess 201c are formed by the push-in roll and to what extent the wave-forming is performed can be determined as appropriate, but in the usual case, it is desirable that the pushing depth 91d of the first sheet 201 by the push-in pin 91 be 2 to 10 mm, the wave height 81h in wave-forming by the wave-forming device 81 be 1 to 8 mm, and the peak-to-peak interval 81d of the adjacent waves in the CD be 1 to 5 mm The first sheet 201 on which the receiving recesses 201c is formed is rotated to the feeding position of the next particulate material feeding device 100 while being wound around the anvil roll 70. At this time, since the concaves 71 are located in the suction compartment 55G from the stage of forming the receiving recesses 201c, and the concaves 71 are continuously sucked, the receiving recesses 201c are firmly held in the concaves 71 while the receiving recesses remain their formed shapes. The sucking is continued at least to the second sheet 202 feeding position, preferably to the welding position. As illustrated in FIGS. 13 and 22, the particulate materials 203 are dropped and fed to each receiving recess 201c of the first sheet 201 from the particulate material feeding device 100. The particulate materials 203 can be continuously fed or intermittently fed in at least a part in the CD.

Figure 23:
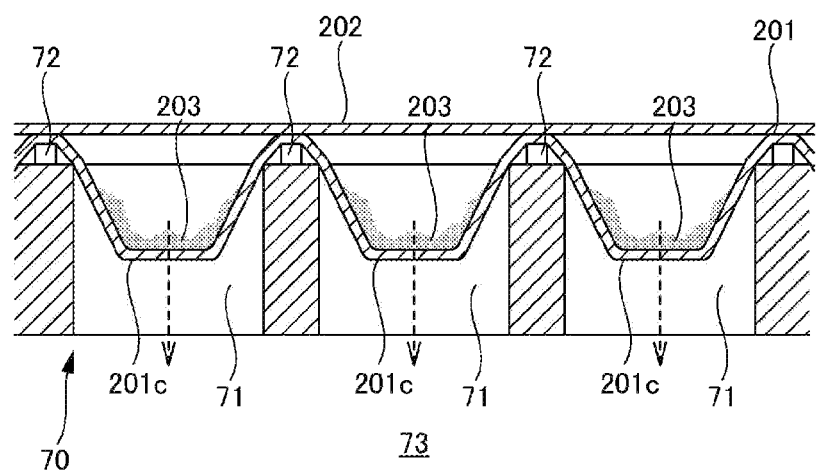
FIG. 23 is an enlarged cross-sectional view of a main part illustrating the second sheet coating process.
Figure 24:
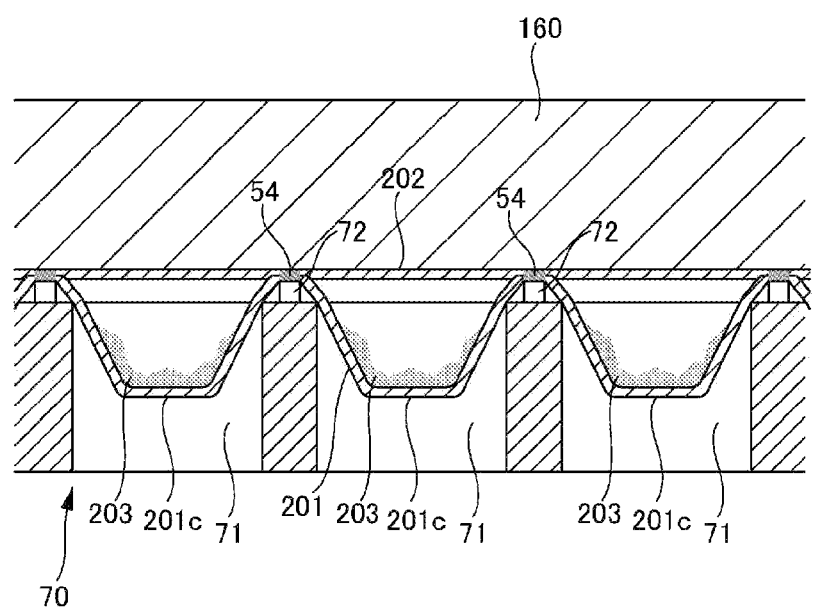
FIG. 24 is an enlarged cross-sectional view of a main part illustrating the welding step.

With respect to the first sheet 201 in which the particulate materials 203 are fed to the receiving recesses 201c, as illustrated in FIGS. 13 and 23, the second sheet 202 is immediately wound around the outside of the first sheet 201 by the second sheet feeding unit 150, and the CD range having at least the receiving recess 201c of the first sheet 201 is covered with the second sheet 202. While the first sheet 201 and the second sheet 202 are wound around the anvil roll 70, as illustrated in FIGS. 13 and 24, by the welding unit 160, portions among the receiving recesses 201c of the first sheet 201 and the second sheet 202 are immediately welded and bonded at sites of the dot-shaped projections 72 on the anvil roll 70 to sequentially form a continuous series 200 of the absorbers 50 in which a large number of the cells 55 containing the particulate materials 203 are arranged. After delivering the continuous series 200 of the absorbers 50 from the anvil roll 70, it is cut into individual absorbers 50 at intervals in the MD by a cutting device (not illustrated).

The projections 72 of the anvil roll 70 can be formed in an appropriate pattern, but as illustrated in FIGS. 14A and 14B, the dot-shaped projections 72 in each of which the area of the tip end surface is 8 mm$^2$ or less (larger than 0 mm$^2$) and the width 72W in the direction orthogonal to the direction surrounding each concave 71 is 4 mm or less (longer than 0 mm) are arranged in only one row at intervals 72D in the direction surrounding each concave 71. The peripheral edge of each receiving recess 201c in the first sheet 201 preferably coincides with the edges on the receiving recess 201c side of the dot-shaped projections 72 surrounding the each receiving recess 201c. The projections 72 are provided for forming the bonded portions 54 in a product, and their arrangement and dimension can be made almost the same as the bonded portions 54 in the product.

In this way, on the outer peripheral surface of the anvil roll 70 for bonding the first sheet 201 and the second sheet 202 by welding, prior to bonding, formation of the receiving recesses 201c of the first sheet 201, feeding of the particulate materials 203, and covering with the second sheet 202 are performed. At least from feeding of the particulate materials 203 to covering with the second sheet 202, a basic mode is carried out where the inside of each concave 71 of the anvil roll 70 is suctioned. As illustrated in FIGS. 14A and 14B and 22, the projections 72 of the anvil roll 70 are intentionally set to small dot-shaped projections 72 and for each concave 71, arranged in one row at intervals in the direction surrounding the concave 71 in the portion among the concaves 71. The peripheral edge of each receiving recess 201c in the first sheet 201 coincides with the edges on the receiving recess 201c side of the dot-shaped projections 72 surrounding the receiving recess 201c. In this case, since the projections 72 have small dot shapes, it is basically difficult for the particulate materials 203 to be placed on the positions overlapping with the projections 72 of the anvil roll 70 in the first sheet 201. In addition, since the receiving recesses 201c formed in the first sheet 201 become the receiving recesses 201c which are inclined from the inner edges 72e of the projections 72 surrounding the concaves 71, the particulate materials 203 easily drop in the receiving recesses 201c by suction force indicated by the dotted arrows in FIG. 22, and the particulate materials 203 in the receiving recesses 201c are likely to move to deeper positions. Furthermore, for each receiving recess 201c, in the portion between each pair of the dot-shaped projections 72 adjacent to each other in the direction surrounding the concave 71, the first sheet is inclined toward the low point at the center of the adjacent projections and inclined toward the receiving recesses 201c on the both sides of the portion (like a ridge of connected mountains), such that the particulate materials 203 positioned in the dot-shaped projections 72 or in the vicinity thereof are more likely to move toward the inside of the receiving recesses 201c by the suction force. Therefore, when the first sheet 201 and the second sheet 202 are bonded by welding in a simple technique of changing the pattern of the projections 72 of the anvil roll 70, which makes it harder for the particulate materials 203 to get caught between the sheets at the bonded portions 54, and bonding failure of the sheets can be effectively prevented.

Although the feeding position by the particulate material feeding device 100 is adjusted appropriately, as illustrated in FIG. 13, it is desirable that the particulate materials 203 be dropped within a range in which the rotation angle.theta.1 with the vertically upward direction as 0.degree. is 30.degree. or more (more preferably 45.degree. or more) in the rotation direction of the anvil roll 70, and the angle.theta.2 formed by the horizontal plane and the ridge line positioned on the most downstream side in the rotation direction of the receiving recess 201c of the first sheet 201 is 0.degree. or more (more preferably 10.degree. or more). When the particulate materials 203 are dropped and fed onto the first sheet 201 at such a position, even if the particulate materials 203 drop to a position corresponding to the projection 72 of the anvil roll 70 in the first sheet 201, the particulate materials are likely to drop on the downstream side in the rotation direction, such that the particulate materials 203 do not easily stay at the position corresponding to the projection 72. Further, the receiving recess 201c is oriented sideways, which makes difficult to cause a situation in which the particulate materials 203 in the receiving recess 201c move to the position corresponding to the projection 72 of the anvil roll 70.

Figure 28:
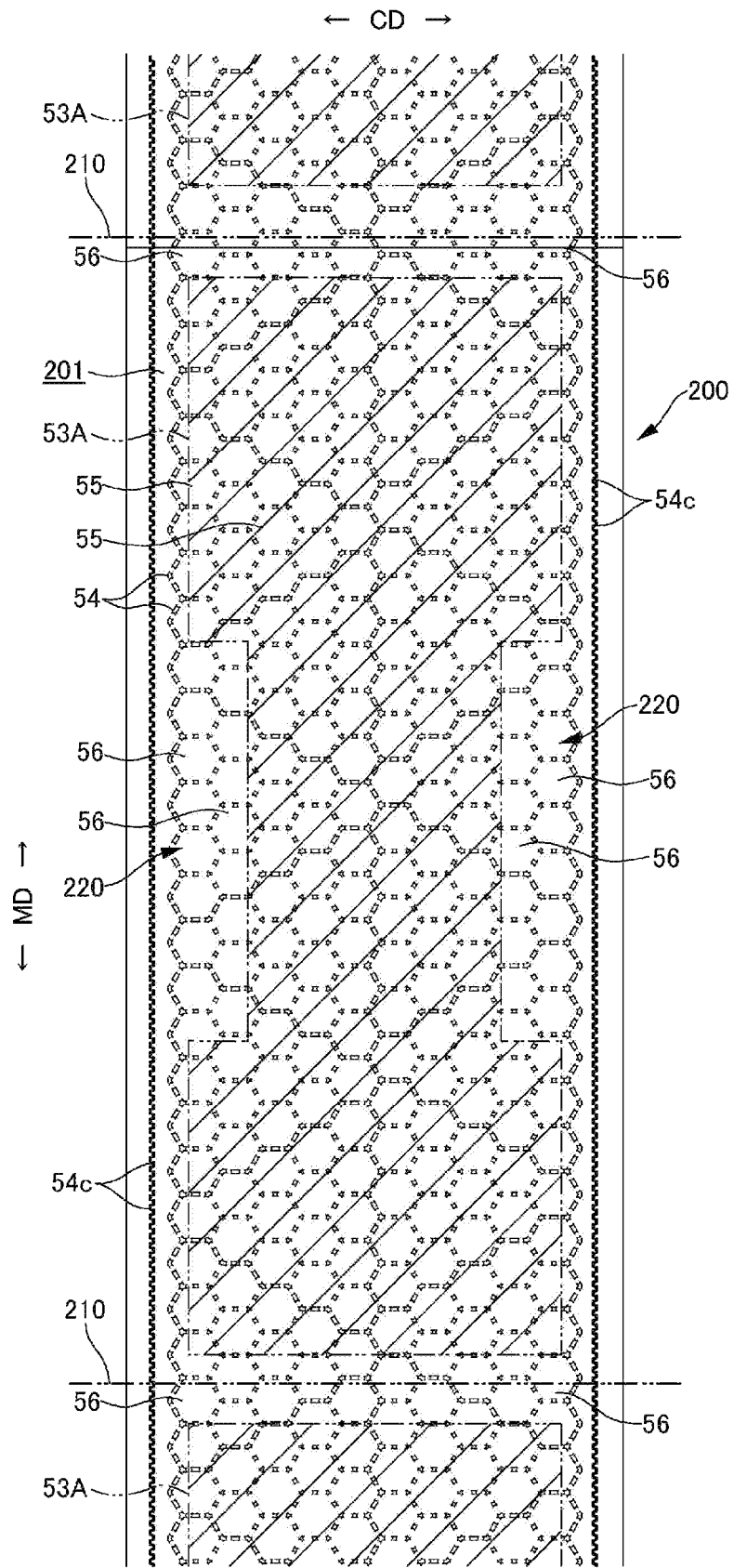
FIG. 28 is a plan view of a continuous series of absorbers.

In addition, when the above-described particulate material feeding device 100 is used, it is possible to feed the following particulate materials 203. That is, when the feeding position of the particulate material feeding device 100 is positioned in the intermediate portion in the MD between the receiving recesses 201c overlapping with each pair of the planned-cutting-positions into the individual absorbers 50 in the first sheet 201, the timing for the first blocking body 104 to intermittently enter the first blocking position is set so as to block feeding of the particulate materials 203 by the first blocking body 104. When the feeding position of the particulate material feeding device 100 includes the receiving recesses 201c overlapping with the planned-cutting-position into the individual absorbers 50 in the first sheet 201, the timing for the second blocking body 105 to enter the second blocking position is set so as to block feeding of the particulate materials 203 by the second blocking body 105. As a result, as illustrated in FIG. 28, in the continuous series 200 of the absorbers 50 to be manufactured, the cells 55 overlapping with each pair of the planned-cutting-positions 210 to the individual absorbers 50 are the empty cells 56 containing no particulate materials 203 including the superabsorbent polymer particles 53, and therefore it is possible to prevent shortening the life of a blade of the cutting device. Also, in the continuous series 200 of the absorbers 50, the cells 55 at the positions 220 along the legs on the both sides in the intermediate portion in the front-back direction LD are also the empty cells 56 containing no particulate materials 203 including the superabsorbent polymer particles 53. Therefore, the portions are less swollen even after absorption, and even after the absorption, the absorber 50 is shaped to fit around the legs.

<Others>

Although the particulate material feeding device 100 of the above example is used for feeding the particulate materials 203 including the superabsorbent polymer particles in manufacturing the cell absorbers 50, it can be also used in the case where layers of particles such as superabsorbent polymer particles are laminated on the assembly of pulp fibers, a sheet of a nonwoven fabric or the like. Further, the particulate material feeding device 100 of the above example can be used in the case of using particulate materials other than superabsorbent polymer particles such as deodorant particles instead of or together with the superabsorbent polymer particles, in the case of the particulate materials 203 that can be dropped and fed, and it can be generally applied to the feeding of the particulate materials 203.

Explanation of Terms Used Herein

In the case where the following terms are used in the specification, those have the following meanings unless otherwise specified in the specification.

"Machine direction (MD)" and "cross direction (CD)" mean the flow direction (MD) in a manufacturing facility and the lateral direction (CD) orthogonal to the flow direction, and either one is the front-back direction of a product, and the other is the width direction of the product. The MD of a nonwoven fabric is the direction of fiber orientation of the nonwoven fabric. "Fiber orientation" is a direction along which a fiber of a nonwoven fabric runs and determined by, for example, a measurement method in accordance with the fiber orientation test method based on the zero span tensile strength of TAPPI T481 and a simple measurement method for determining the direction of the fiber orientation from the ratio of the tensile strength in the front-back direction to the width direction.

"Spread state" means a flatly spread state without contraction or slack.

"Stretch rate" means the value when the natural length is taken as 100%.

"Artificial urine" is prepared by mixing urea: 2 wt %, sodium chloride: 0.8 wt %, calcium chloride dihydrate: 0.03 wt %, magnesium sulfate heptahydrate: 0.08 wt %, and ion exchanged water: 97.09 wt %, and those are used at a temperature of 40.degree. C. unless otherwise specified.

"Gel strength" is measured as follows: 1.0 g of superabsorbent polymers are added to 49.0 g of artificial urine and the mixture is stirred with a stirrer. The resulting gel is left for three hours in a thermohygrostat bath at 40.degree. C., 60% RH and then cooled to room temperature. The gel strength of the gel is measured with Curdmeter (MAX ME-500, manufactured by I. Techno Engineering Co., Ltd).

"Basis weight" is measured as follows. After the sample or test piece is preliminarily dried, it is allowed to stand in a test room or apparatus under normal conditions (the test location is at a temperature: 20.+−0.5.degree. C., relative humidity: 65% or less) until the constant mass. The preliminary drying is to make the sample or test piece be constant mass in an environment within a relative humidity of 10 to 25% and at a temperature not exceeding 50.degree. C. The fibers of an official moisture regain of 0.0% does not need preliminary drying. A cut sample with a size of 200 mm by 250 mm (.+−0.2 mm) is cut from the test piece in the constant mass, with a cutting template (200 mm.times.250 mm, .+−0.2 mm). The sample is weighed and the weight is multiplied by 20 into the weight per square meter. The resulting value is defined as the basis weight. "Thickness" is automatically measured under the conditions of a load of 10 gf/cm.sup.2 in a pressurized area of 2 cm.sup.2 using an automatic thickness measuring device (KES-G5 handy compression tester).

"Water absorption capacity" is measured according to JIS K7223-1996 "Testing method for water absorption capacity of super absorbent polymers".

"Water absorption rate" is the "time that elapses before the end point" measured in accordance with JIS K7224-1996 "Testing method for water absorption rate of super absorbent polymers" has been carried out using 2 g of superabsorbent polymers and 50 g of physiological saline solution.

When environmental conditions in tests and measurements are not described, the tests and measurements shall be carried out in a test room or apparatus under normal conditions (the test location is at a temperature: 20.+−0.5.degree. C., relative humidity: 65% or less).

The dimension of each part means the dimension in the spread state, not the natural length state, unless otherwise stated.

REFERENCE SIGNS LIST 11 liquid impervious sheet
12 outer sheet
12T target sheet
13 fastening tape
13A engagement portion
13B tape main unit section
13C tape attaching portion
30 top sheet
40 intermediate sheet
60 three-dimensional side gather
62 gather sheet
50 absorber
51 front surface side sheet
51c recess
52 back surface side sheet
53 superabsorbent polymer particles
54 bonded portion
54a strong bonded portion
54b weak bonded portion
54c edge bonded portion
55 cell
55G compartment
WD width direction
56 empty cell
70 anvil roll
71 concave
72 projection
80 first sheet feeding unit
81 wave-forming device
82 groove roll
83 convex roll
90 recess forming unit
91 push-in pin
100 particulate material feeding device
150 second sheet feeding unit
151 guide plate
160 welding unit
201 first sheet
202 second sheet
201c receiving recess
203 particulate materials
101 particulate material storage tank
102 delivery device
103 chute
104, 105 blocking body
104 first blocking body
105 second blocking body
106 recovery path
121 chute feeding port
115 chute discharge port
116 partition plate
210 cutting position

The invention claimed is:

1. A device for manufacturing an absorber, comprising:
an anvil roll driven around a transverse rotational axis in a rotation direction, the anvil roll having an outer peripheral portion that defines an inner space; wherein a plurality of concave regions are formed at intervals in the outer peripheral portion and a plurality of projections extend from the outer peripheral portion and surround each of the plurality of concave regions, and wherein a suction unit is located in the inner space and is configured to suck air from the plurality of concave regions, and
wherein the device further comprises a first sheet feeding unit comprising a guide roll and a drive roll, a receiving recess forming unit, a particulate material feeding device, a second sheet feeding unit and a welding unit in this order from an upstream side to a downstream side in the rotation direction of the anvil roll;
wherein the first sheet feeding unit is configured to feed a continuous belt-shaped first sheet made of a liquid pervious nonwoven fabric in the rotation direction of the anvil roll along the outer peripheral portion of the anvil roll such that the continuous belt-shaped first sheet is wound around the anvil roll; the first sheet feeding unit further comprising:
- a groove roll having a plurality of grooves that are continuous in a roll circumferential direction and arranged in a roll length direction on an outer peripheral surface of the groove roll;
- a convex roll having a plurality of convex portions that are continuous in a roll circumferential direction and arranged in a roll length direction on an outer peripheral surface of the convex roll, wherein the groove roll and the convex roll are opposed to each other such that the plurality of grooves and the plurality of convex portions are engaged with each other, and
- a heating unit configured to heat the first sheet to a melting temperature or lower as the first sheet is stretched between the groove roll and the convex roll to form a wave pattern in the first sheet;

wherein the receiving recess forming unit is configured to form receiving recesses in the first sheet along the outer peripheral portion of the anvil roll, the receiving recesses being recessed in the plurality of concave regions;

wherein the particulate material feeding device is configured to drop and feed particulate materials including superabsorbent polymer particles from above to the receiving recesses of the first sheet wound around the anvil roll;

wherein the second sheet feeding unit is configured to feed a continuous belt-shaped second sheet in the rotation direction of the anvil roll, wind the second sheet around an outer side of the first sheet, and cover at least a portion in a cross direction having the receiving recesses of the first sheet, with the second sheet;

wherein the welding unit is configured to weld the first sheet and the second sheet only at the plurality of projections while winding the first sheet and the second sheet around the anvil roll; and
- wherein the suction unit sucks air from the plurality of concave regions at least in a region of the outer peripheral portion in the rotation direction from a feeding position of the particulate materials to a feeding position of the second sheet.

2. The device for manufacturing an absorber according to claim 1, wherein a rotation angle formed between the feeding position of the particulate materials by the particulate material feeding device and a vertically upward direction is 30° or more, and an angle formed by a horizontal plane and a ridge line positioned on a most downstream side in a rotation direction of a receiving recess in the feeding position of the particulate materials of the first sheet is 0° or more.

3. The device for manufacturing an absorber according to claim 1, wherein the receiving recess forming unit comprises a pushing roll which is opposed to the anvil roll, the pushing roll having a plurality of push-in pins for entering the plurality of concave regions of the anvil roll,
- wherein the first sheet is passed in the rotation direction of the anvil roll between the anvil roll and the pushing roll, and
- wherein the first sheet is pushed into the plurality of concave regions with the plurality of push-in pins to form the receiving recesses in the first sheet.

4. The device for manufacturing an absorber according to claim 3, wherein a rotation angle formed between the feeding position of the particulate materials by the particulate material feeding device and a vertically upward direction is 30° or more, and an angle formed by a horizontal plane and a ridge line positioned on a most downstream side in a rotation direction of a receiving recess in the feeding position of the particulate materials of the first sheet is 0° or more.

5. The device for manufacturing an absorber according to claim 3, wherein a pushing depth of the first sheet by the plurality of push-in pins is 2 to 10 mm, and wherein a wave height of the wave pattern is 1 to 8 mm, and a peak-to-peak interval of the wave pattern in the cross direction is 1 to 5 mm.

6. The device for manufacturing an absorber according to claim 5, wherein a rotation angle formed between the feeding position of the particulate materials by the particulate material feeding device and a vertically upward direction is 30° or more, and an angle formed by a horizontal plane and a ridge line positioned on the most downstream side in a rotation direction of a receiving recess in the feeding position of the particulate materials of the first sheet is 0° or more.

7. A method for manufacturing absorbers using a manufacturing device which comprises:
- an anvil roll driven around a transverse rotational axis in a rotation direction, the anvil roll having an outer peripheral portion that defines an inner space; wherein a plurality of concave regions are formed at intervals in the outer peripheral portion and a plurality of projections extend from the outer peripheral portion and surround each of the plurality of concaves regions, and wherein a suction unit is located in the inner space and is configured to suck air from the plurality of concaves regions; and
- wherein the device further comprises a first sheet feeding unit comprising a guide roll and a drive roll, a receiving recess forming unit, a particulate material feeding device, a second sheet feeding unit and a welding unit in this order from an upstream side to a downstream side in the rotation direction of the anvil roll;

wherein the first sheet feeding unit is configured to feed a continuous belt-shaped first sheet made of a liquid pervious nonwoven fabric in the rotation direction of the anvil roll along the outer peripheral portion of the anvil roll such that the continuous belt-shaped first sheet is wound around the anvil roll; the first sheet feeding unit further comprising:
- a groove roll having a plurality of grooves that are continuous in a roll circumferential direction and arranged in a roll length direction on an outer peripheral surface of the groove roll;
- a convex roll having a plurality of convex portions that are continuous in a roll circumferential direction and arranged in a roll length direction on an outer peripheral surface of the convex roll, wherein the groove roll and the convex roll are opposed to each other such that the plurality of grooves and the plurality of convex portions are engaged with each other, and
- a heating unit configured to heat the first sheet to a melting temperature or lower as the first sheet is stretched between the groove roll and the convex roll to form a wave pattern in the first sheet;

wherein the receiving recess forming unit is configured to form receiving recesses in the first sheet along the outer peripheral portion of the anvil roll, the receiving recesses being recessed in the plurality of concaves regions;

wherein the particulate material feeding device is configured to drop and feed particulate materials including superabsorbent polymer particles from above to the receiving recesses of the first sheet wound around the anvil roll;

wherein the second sheet feeding unit is configured to feed a continuous belt-shaped second sheet in the rotation direction of the anvil roll, wind the second sheet around an outer side of the first sheet, and cover at least a portion in a cross direction having the receiving recesses of the first sheet, with the second sheet;

wherein the welding unit is configured to weld the first sheet and the second sheet only at the plurality of projections while winding the first sheet and the second sheet around the anvil roll; and wherein the suction unit sucks air from the plurality of concave regions at least in a region of the outer peripheral portion in the rotation direction from a feeding position of the particulate materials to a feeding position of the second sheet;

the method comprising:

feeding the first sheet to the anvil roll by the first sheet feeding unit;

forming the receiving recesses on the first sheet by the receiving recess forming unit;

feeding the particulate materials to the receiving recesses of the first sheet by the particulate material feeding device;

overlapping the second sheet on the first sheet by the second sheet feeding unit;

bonding the portions among the receiving recesses of the first sheet and the second sheet by the welding unit to successively form a continuous series of absorbers in which a plurality of cells containing the particulate materials are arranged; and cutting the continuous series of the absorbers into individual absorbers at intervals in a machine direction that is orthogonal to the cross direction.

* * * * *

UNITED STATES PATENT AND TRADEMARK OFFICE
CERTIFICATE OF CORRECTION

PATENT NO. : 11,020,283 B2  
APPLICATION NO. : 16/088916  
DATED : June 1, 2021  
INVENTOR(S) : Sadanao Manabe and Ryoichi Ochi Page 1 of 1

It is certified that error appears in the above-identified patent and that said Letters Patent is hereby corrected as shown below:

In the Claims

Column 28, Line 31 of Claim 7:  
"…plurality of concaves regions…"  
Should instead read:  
-- …plurality of concave regions… --

Column 28, Line 33 of Claim 7:  
"…plurality of concaves regions…"  
Should instead read:  
-- …plurality of concave regions… --

Column 28, Line 66 of Claim 7:  
"…plurality of concaves regions…"  
Should instead read:  
-- …plurality of concave regions… --

Signed and Sealed this  
Twentieth Day of July, 2021

Drew Hirshfeld  
*Performing the Functions and Duties of the*  
*Under Secretary of Commerce for Intellectual Property and*  
*Director of the United States Patent and Trademark Office*